(12) United States Patent
Messer et al.

(10) Patent No.: US 7,268,117 B2
(45) Date of Patent: Sep. 11, 2007

(54) COMPOSITIONS, KITS, AND METHODS FOR IDENTIFICATION, ASSESSMENT, PREVENTION, AND THERAPY OF ENDOMETRIOSIS

(75) Inventors: Jeffrey Messer, Townsend, MA (US); Dennis Benjamin, Redmond, WA (US); James Vath, Lynnfield, MA (US); Eric Sigel, Brookline, MA (US)

(73) Assignee: Praecis Pharmaceuticals Incorporated, Waltham, MA (US)

( * ) Notice: Subject to any disclaimer, the term of this patent is extended or adjusted under 35 U.S.C. 154(b) by 0 days.

(21) Appl. No.: 10/887,775

(22) Filed: Jul. 9, 2004

(65) Prior Publication Data

US 2005/0130182 A1 Jun. 16, 2005

Related U.S. Application Data

(60) Provisional application No. 60/575,269, filed on May 28, 2004, provisional application No. 60/533,430, filed on Dec. 29, 2003, provisional application No. 60/486,379, filed on Jul. 11, 2003.

(51) Int. Cl.
*A61K 38/00* (2006.01)

(52) U.S. Cl. .......................................... 514/12
(58) Field of Classification Search .................. 514/12; 530/350
See application file for complete search history.

(56) References Cited

U.S. PATENT DOCUMENTS

| 5,474,927 | A | | 12/1995 | Anderson et al. |
| 5,478,725 | A | * | 12/1995 | Lessey ...................... 435/7.21 |
| 5,618,689 | A | | 4/1997 | McCarthy et al. |
| 5,843,673 | A | | 12/1998 | Sharpe-Timms |
| 6,525,187 | B1 | | 2/2003 | El Shami et al. |
| 2002/0127555 | A1 | * | 9/2002 | Baban et al. .................. 435/6 |
| 2003/0124551 | A1 | | 7/2003 | Pappa et al. |

FOREIGN PATENT DOCUMENTS

| EP | 1191107 A2 | | 3/2002 |
| WO | WO95/13821 A1 | | 5/1995 |
| WO | WO96/20404 A1 | | 7/1996 |
| WO | WO99/55902 A1 | | 11/1999 |
| WO | WO99/63116 A2 | | 12/1999 |
| WO | WO99/63116 A3 | | 12/1999 |
| WO | WO 00/47739 A2 | | 8/2000 |
| WO | WO 00/47739 A3 | | 8/2000 |
| WO | WO 00/63675 | * | 10/2000 |
| WO | WO 00/63675 A1 | | 10/2000 |
| WO | WO 01/62959 A2 | | 8/2001 |
| WO | WO 01/62959 A3 | | 8/2001 |

OTHER PUBLICATIONS

Increased Expression of complement component 3 in human ectopic endometrium compared with the matched eutopic endometrium, Fertility and Sterlity, vol. 68, Sep. 1997, pp. 460-467.*

* cited by examiner

*Primary Examiner*—Karen Cochrane Carlson
*Assistant Examiner*—Agnes B. Rooke
(74) *Attorney, Agent, or Firm*—Lahive & Cockfield, LLP; Giulio A. DeConti; Maria Laccotripe Zacharakis

(57) ABSTRACT

The invention relates to newly discovered marker polypeptides associated with endometriosis. Compositions, kits, and methods for detecting, characterizing, preventing, and treating endometriosis are provided.

8 Claims, 6 Drawing Sheets

COMPOSITIONS, KITS, AND METHODS FOR IDENTIFICATION, ASSESSMENT, PREVENTION, AND THERAPY OF ENDOMETRIOSIS

RELATED APPLICATIONS

The present application claims priority from U.S. provisional patent application Ser. No. 60/575,269, filed on May 28, 2004, U.S. provisional patent application Ser. No. 60/486,379, filed on Jul. 11, 2003, and from U.S. provisional patent application Ser. No. 60/533,430, filed on Dec. 29, 2003, which are expressly incorporated herein by reference.

BACKGROUND OF THE INVENTION

Endometriosis is a condition afflicting women of childbearing age which is characterized by the growth of endometrial tissue in areas outside the uterus. These extrauterine endometrial growths are a leading cause of pelvic pain and can also cause infertility. Endometrial growths can occur in a variety of locations, including the lining of the pelvic cavity and the outer surface of the uterus, and can also occur outside the abdomen, for example, in the lung.

As is the case with the uterine lining, extrauterine endometrial growths typically respond to the varying levels of estrogen associated with the menstrual cycle. Thus, endometrial growths proceed through a cycle of proliferation and breakdown. Unlike the uterine lining, however, the body is unable to shed the extrauterine endometrial growths, and breakdown of this tissue results in internal bleeding, inflammation of the surrounding area and formation of scar tissue. A number of complications can also arise, including rupture of growths, which can spread the growths to new regions of the body, and the formation of adhesions.

The most common symptoms of endometriosis include constant pelvic pain, infertility, low sacral backache, and heavy or irregular bleeding. The degree of pain does not correspond to the size or extent of endometrial growths, and significant pain can result even from microscopic growths. Endometrial implants can destroy ovarian and tubal tissue. Several disorders of menstrual cyclicity and ovulation have been suggested as a basis for the infertility caused by mild endometriosis. More subtle problems in folliculogenesis in endometriosis patients have been reported, including lower serum estradiol levels, smaller follicle size during follicular growth, and lower oocyte fertilization rates and pregnancy rates in assisted reproduction. Problems with ovum pickup by the fallopian tube and embryo implantation in the endometrium have also been suggested.

Currently, a definitive diagnosis of endometriosis can be made only upon laparoscopic examination of the abdomen. This is a surgical procedure performed under local anesthesia and can indicate the extent and location of extrauterine endometrial growths. Laparoscopic examination is essential because symptoms of endometriosis are similar to the symptoms of other conditions, including ovarian cancer. Prevention of endometriosis is not currently possible; however, treatment options are available based on the patient's desire for future fertility, symptoms, the stage of disease, and to some extent, age. Possible treatment options include analgesic treatments, such as nonsteroidal anti-inflammatory agents and prostaglandin synthetase-inhibiting drugs, and hormonal therapy, which may be given as a means for interrupting the cycles of stimulation and bleeding of endometriotic tissue. Common hormonal therapies include oral contraceptive pills; progestational agents, which cause decidualization in the endometriotic tissue; danazol, a weak androgen that is the isoxazole derivative of 17α-ethinyl testosterone (ethisterone); and gonadotropin-releasing hormone (GnRH) agonists, which are analogues of the 10-amino-acid polypeptide hormone GnRH and act via the suppression of gonadotropin secretion, resulting in elimination of ovarian steroidogenesis and suppression of endometrial implants. Lastly, surgical treatment, including laparoscopic resection, ablation of minimal or mild endometriosis, presacral neurectomy and uterosacral ligament ablation, may be performed to excise or destroy all endometriotic tissue, remove all adhesions, and restore pelvic anatomy to the best possible condition.

Despite the treatments available for endometriosis, it would be beneficial to provide specific non-invasive methods and reagents for the diagnosis, staging, prognosis, monitoring, and treatment of endometriosis and endometriosis-related diseases, or to indicate a predisposition to such for preventative measures.

SUMMARY OF THE INVENTION

The invention relates to markers (hereinafter "markers", "marker polypeptides" or "markers of the invention"), which are listed in Tables 1–3. The invention provides nucleic acids and polypeptides that encode or correspond to the markers (hereinafter "marker nucleic acids" and "marker polypeptides," respectively). Tables 1–3 provide the sequence identifiers of the sequences of such marker peptides listed in the accompanying Sequence Listing. The invention further provides antibodies, antibody derivatives and antibody fragments which bind specifically with the marker polypeptides and/or fragments of the marker polypeptides.

Table 1 lists all of the markers of the invention, whose over- or under-abundance may be correlated with the diagnosis and prognosis of endometriosis. In particular, Table 1 provides the name of the gene corresponding to the marker ("Gene Name"), the amino acid sequence ("Sequence") and the sequence listing identifier of the amino acid sequence of the polypeptide marker ("SEQ ID NO (AAs)"). Table 2 lists markers whose over-abundance may be correlated with endometriosis as compared to normal samples from control subjects that do not have endometriosis. Table 3 lists markers whose under-abundance may be correlated with endometriosis as compared to normal samples from control subjects that do not have endometriosis.

The invention also relates to various methods, reagents and kits for diagnosing, staging, prognosticating, monitoring and treating endometriosis. "Endometriosis" as used herein includes a disorder in which abnormal growth of tissue, histologically resembling the endometrium, is present in locations other than the uterine lining (see Ainbinder et al., *Current Obstetric & Gynecologic Diagnosis & Treatment*, 9th ed., Lange Medical Books/McGraw-Hill, 2003). As used herein, an "endometriosis-related disease" (also referred to herein as a "disorder" or "condition") may include a disease, disorder, or condition, whose onset was related to endometriosis. Such diseases, disorders and conditions include infertility, and abdominal and/or pelvic pain.

In one embodiment, the invention provides a diagnostic method of assessing whether a patient has endometriosis or has higher than normal risk for developing endometriosis, comprising the steps of comparing the abundance of a marker of the invention in a patient sample and the normal abundance of the marker in a control, e.g., a sample from a subject that does not have endometriosis. A difference in the abundance of the marker in the patient sample, as compared to the normal abundance, is an indication that the patient is afflicted with endometriosis or has higher than normal risk for developing endometriosis.

The methods of the present invention can be of use in identifying patients having an enhanced risk of developing endometriosis (e.g., patients having a familial history of endometriosis and patients identified as having altered abundance of a marker of the invention). The methods of the present invention may further be of particular use in evaluating the specific stage of endometriosis, as well as in assessing the progression of the disease. The methods of the present invention are also useful in predicting the clinical outcome for a patient with endometriosis, or for a patient who has undergone therapy to eradicate endometriosis. The methods of the present invention are also useful in assessing the efficacy of treatment of a patient diagnosed with endometriosis (e.g., the efficacy of hormonal suppression or surgical ablation of endometrial implants).

The markers of the invention set forth in Table 1 may be used in the methods of the invention. It will be appreciated that in the methods of the invention, over-abundance of the markers set forth in Table 2 in the patient sample may be correlated with endometriosis as compared to normal samples from control subjects. Likewise, in the methods of the invention, under-abundance of the markers set forth in Table 3 in the patient sample may be correlated with endometriosis as compared to normal samples from control subjects.

In a preferred diagnostic method of assessing whether a patient is afflicted with endometriosis (e.g., new detection ("screening"), detection of recurrence), the method comprises comparing:
  a) the abundance of a marker listed in Table 1 in a sample from the patient, and
  b) the normal abundance of the marker.

A different abundance of the marker in the patient sample, as compared to the level in the control subject, i.e., increased or decreased as specified in Tables 2–3, is an indication that the patient is afflicted with endometriosis.

The invention additionally provides a diagnostic method for assessing the aggressiveness of endometriosis, the method comprising comparing:
  a) the abundance of a marker listed in Table 1 in a sample from the patient, and
  b) the normal abundance of the marker.

A different abundance in the patient sample, as compared to the normal level, i.e., increased or decreased as specified in Tables 2–3, is an indication that the patient has an aggressive form of endometriosis or is likely to develop endometriosis.

The invention also provides methods for assessing the efficacy of a therapy for inhibiting endometriosis in a patient. Such methods comprise comparing:
  a) the abundance of a marker of the invention in a first sample obtained from the patient prior to providing at least a portion of the therapy to the patient, and
  b) the abundance of the marker in a second sample obtained from the patient following provision of the portion of the therapy.

An altered abundance of the marker in the second sample relative to that in the first sample, i.e., increased or decreased as specified in Tables 2–3, is an indication that the therapy is efficacious for inhibiting endometriosis in the patient.

It will be appreciated that in the methods of the present invention, the "therapy" may be any therapy for treating endometriosis including, but not limited to, analgesic treatments, hormone therapy, surgical removal of endometrial implants, gene therapy and biologic therapy such as the administering of antibodies. Thus, the methods of the invention may be used to evaluate a patient before, during and after therapy, for example, to evaluate the reduction in endometriosis due to the therapy.

In a preferred embodiment, the methods are directed to therapy using a chemical or biologic agent. These methods comprise comparing:
  a) the abundance of a marker of the invention in a first sample obtained from the patient and maintained in the presence of the chemical or biologic agent, and
  b) the abundance of the marker in a second sample obtained from the patient and maintained in the absence of the agent.

An altered abundance of the marker in the second sample relative to that in the first sample, i.e., increased or decreased as specified in the above-described methods and in Tables 2–3, is an indication that the agent is efficacious for inhibiting endometriosis, in the patient. In one embodiment, the first and second samples can be portions of a single sample obtained from the patient or portions of pooled samples obtained from the patient.

The invention additionally provides a monitoring method for assessing the progression of endometriosis in a patient, the method comprising:
  a) detecting in a sample from the patient at a first time point, the abundance of a marker of the invention;
  b) repeating step a) at a subsequent time point in time; and
  c) comparing the abundance detected in steps a) and b), and therefrom monitoring the progression of endometriosis in the patient.

A different abundance of the marker in the sample at the subsequent time point from that of the sample at the first time point, i.e., increased or decreased as specified in the above-described methods and in Tables 2 and 3, is an indication that the endometriosis has progressed or regressed in the patient.

The invention moreover provides a test method for selecting a composition for inhibiting endometriosis in a patient. This method comprises the steps of:
  a) obtaining a sample from the patient;
  b) separately maintaining aliquots of the sample in the presence of a plurality of test compositions;
  c) comparing the abundance of a marker of the invention in each of the aliquots; and
  d) selecting one of the test compositions which significantly alters the abundance of the marker in the aliquot containing that test composition, relative to the abundance of the marker in the presence of the other test compositions.

In addition, the invention further provides a method of inhibiting endometriosis in a patient. This method comprises the steps of:
  a) obtaining a sample from the patient;
  b) separately maintaining aliquots of the sample in the presence of a plurality of compositions;
  c) comparing the abundance of a marker of the invention in each of the aliquots; and
  d) administering to the patient at least one of the compositions which significantly alters the abundance of the marker in the aliquot containing that composition, relative to the abundance of the marker in the presence of the other compositions.

In the aforementioned methods, the samples or patient samples comprise cells, tissues and/or fluids obtained from the patient. The cells may be found in a cervical smear collected, for example, by a cervical brush. In another embodiment, the sample is a body fluid. Such fluids include, for example, blood fluids, serum, plasma, a blood fraction, lymph, ascitic fluids, gynecological fluids, urine, peritoneal fluid, cerebrospinal fluid, and fluids collected by vaginal rinsing. In a further embodiment, the patient sample is in vivo.

According to the invention, the abundance of a marker of the invention in a sample can be assessed, for example, by detecting the presence in the sample of:
the marker polypeptide (e.g., a polypeptide having one of the sequences of SEQ ID NO (AAs)) or a fragment of the polypeptide (e.g. by using a reagent, such as an antibody, an antibody derivative, an antibody fragment or single-chain antibody, which binds specifically with the protein or protein fragment, or via chromatography with a suitable detector)
a metabolite which is produced directly (i.e., catalyzed) or indirectly by the corresponding marker polypeptide; or
a metabolite of the marker polypeptide.

According to the invention, any of the aforementioned methods may be performed using a plurality (e.g. 2, 3, 5, or 10 or more) of markers of the invention, optionally in combination with endometriosis markers known in the art. In such methods, the abundance within the sample of each of a plurality of markers, at least one of which is a marker of the invention, is compared with the normal abundance of each of the plurality of markers. A significantly altered (i.e., increased or decreased as specified in the above-described methods using a single marker) abundance in the sample of one or more markers of the invention, or some combination thereof, relative to that marker's corresponding normal or control level, is an indication that the patient is afflicted with endometriosis.

In a further aspect, the invention provides an antibody, an antibody derivative, or an antibody fragment, which binds specifically with a marker polypeptide (e.g., a polypeptide having the sequence of any of the SEQ ID NO (AAs)) or a fragment of the polypeptide. The invention also provides methods for making such an antibody, antibody derivative, and antibody fragment. Such methods may comprise immunizing a mammal with a polypeptide comprising the entirety, or a fragment, preferably a segment of 7 or more, more preferably 10 or more, amino acids, of a marker polypeptide (e.g., a polypeptide having the sequence of any of the SEQ ID NO (AAs)), wherein the polypeptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker polypeptide or a fragment of the polypeptide.

In another aspect, the invention relates to various diagnostic and test kits. In one embodiment, the invention provides a kit for assessing whether a patient is afflicted with endometriosis. The kit comprises a reagent for assessing the abundance of a marker or a plurality of markers of the invention. In another embodiment, the invention provides a kit for assessing the suitability of a chemical or biologic agent for inhibiting endometriosis in a patient. Such a kit comprises a reagent for assessing the abundance of a marker of the invention, and may also comprise one or more additional such agents. Such kits comprise an antibody, an antibody derivative, or an antibody fragment, which binds specifically with a marker polypeptide, or a fragment of the polypeptide. Such kits may also comprise a plurality of antibodies, antibody derivatives, or antibody fragments wherein the plurality of such antibody agents binds specifically with a marker polypeptide, or a fragment of the marker polypeptide. In another embodiment, the kit includes one or more synthetic standards and/or internal standards.

It will be appreciated that the methods and kits of the present invention may also include known endometriosis markers. It will further be appreciated that the methods and kits may be used to identify conditions related to endometriosis, such as infertility or abdominal and/or pelvic pain of unknown ideology.

BRIEF DESCRIPTION OF THE DRAWINGS

FIGS. 1 and 2 demonstrate that certain markers of the invention, including fibrinopeptide B derivative (SEQ ID NO:28), full length fibrinopeptide A (SEQ ID NO:3) and fibrinopeptide A fragment (SEQ ID NO:7), are present in higher concentrations in the serum of patients diagnosed with endometriosis as compared to healthy patients that do not have endometriosis.

FIG. 3 demonstrates that a marker of the invention, the fibrinopeptide A derivative (SEQ ID NO:4), is present at higher concentrations in the serum of patients diagnosed with endometriosis as compared to serum of healthy patients that do not have endometriosis or patients diagnosed with polycystic ovarian syndrome (PCOS) and pelvic inflammatory disease (PID).

FIG. 4 demonstrates that certain markers of the invention, thymosin fragments (SEQ ID NOS:42 and 43), are present at lower concentrations in the serum of patients diagnosed with endometriosis, PCOS and PID as compared to serum of healthy patients that do not have endometriosis.

FIG. 5 demonstrates that a marker of the invention, phosphoserine fibrinopeptide A (SEQ ID NO:22), is present at lower concentrations in the serum of healthy patients as compared to serum of patients diagnosed with endometriosis, PCOS or PID.

FIG. 6 demonstrates that a marker of the invention, the internal fibrinogen alpha fragment (SEQ ID NO:29), is present at lower concentrations in the serum of patients diagnosed with endometriosis as compared to healthy patients that do not have endometriosis, PCOS or PID.

DETAILED DESCRIPTION OF THE INVENTION

Figure 1:
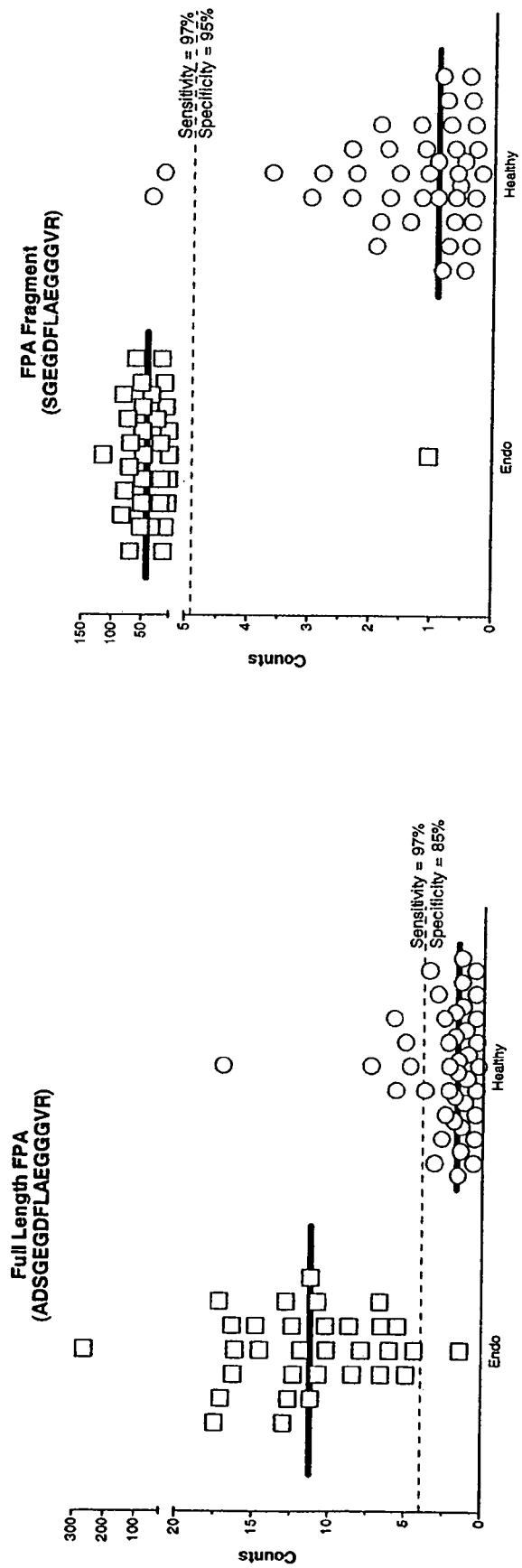
FIGS. 1–6 depict scatter plots showing the concentrations (given as counts) of a given marker in the serum of women diagnosed with endometriosis, the serum of healthy women, and, in certain cases, the serum of women diagnosed with PCOS or PID.
Figure 2:
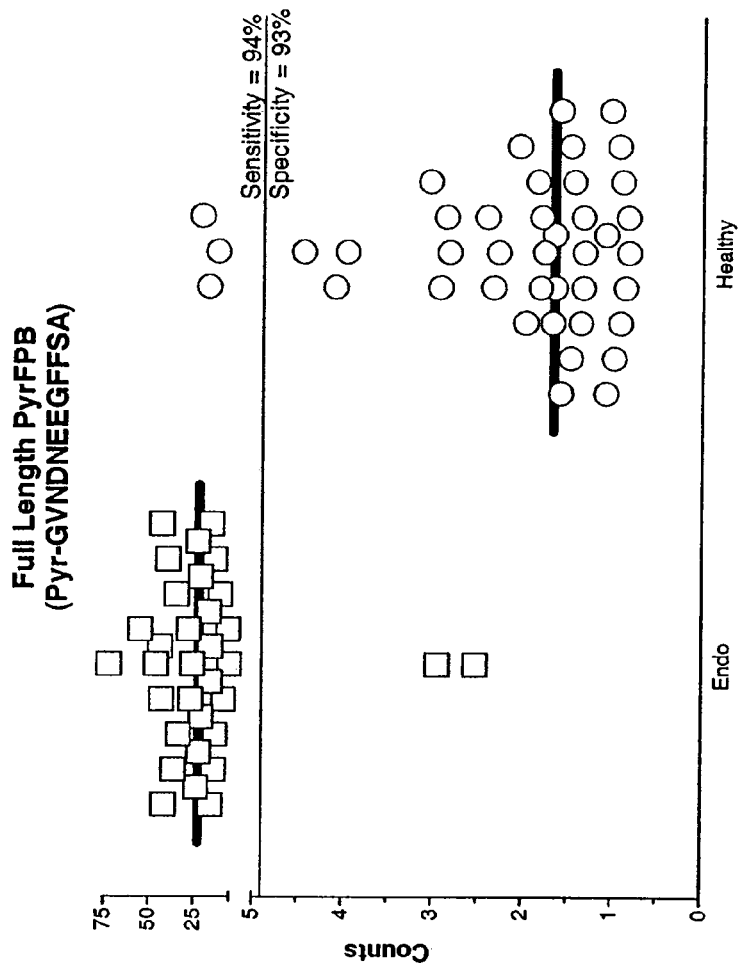
Figure 2:
Figure 2:
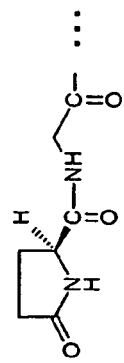

The invention relates to newly discovered markers, whose expression is correlated with the disease state of endometriosis. In particular, the present invention relates to the discovery that patient samples, e.g., serum samples, from women who have endometriosis have higher levels of polypeptides derived from fibrinogen proteolysis than women who do not have endometriosis, as shown either through an absence of signs and symptoms of endometriosis or by another diagnostic method, such as laparoscopy. It has now been found that, compared to women who do not have endometriosis, patient samples, e.g., serum samples, from women who have endometriosis have higher levels of certain markers of the invention and lower levels of certain other markers of the invention. Thus, it has been discovered that for certain markers of the invention an altered, e.g., significantly higher than normal or significantly lower than normal abundance of these markers, or combination of these markers, correlates with the presence of endometriosis in a patient. Methods are provided for detecting the presence or absence of endometriosis in a sample, the stage and progression of endometriosis, predicting the likely clinical outcome of a patient diagnosed with endometriosis, and other characteristics of endometriosis that are relevant to prevention, diagnosis, characterization, and therapy of endometriosis in a patient. Methods of treating endometriosis are also provided.

Table 1 lists all of the markers of the invention, whose over- or under-abundance correlates with endometriosis as compared to normal samples from patients that do not have endometriosis. Table 2 lists markers whose over-expression correlates with endometriosis as compared to normal samples from control subjects. Table 3 lists markers whose under-expression correlates with endometriosis as compared to normal samples from control subjects.

In one embodiment, a marker of the invention is fibrinogen, such as the fibrinogen α (SEQ ID NO:1) or β-chain (SEQ ID NO:2) or a fragment thereof, such as fibrinopeptide A (SEQ ID NO:3), fibrinopeptide B (SEQ ID NO:27) or a fragment thereof (SEQ ID NO:28). The fragment of fibrinopeptide A can be, for example, a fragment derived from N-terminal truncation of fibrinopeptide A (SEQ ID NOS: 5–21). Furthermore, the markers of the invention include fibrinopeptide A and fragments thereof, wherein the serine residue has been converted into dehydroalanine (SEQ ID NO:4) or in which the serine residue is phosphorylated (SEQ ID NOS:22 to 26). In another embodiment, the markers of the invention include fibrinopeptide B (SEQ ID NO:27) and derivatives and fragments thereof, including des-arginine-L-pyroglutamic acid fibrinopeptide B (SEQ ID NO:28). In a further aspect, the markers of the invention include an internal fragment of the fibrinogen α chain, such as a polypeptide having the sequence set forth in (SEQ ID NO:29).

The markers of the invention also include polypeptides derived from Complement component 3 (Complement C3) (SEQ ID NO:30). Complement C3 is converted by the enzyme C3 convertase to two protein products, C3a (SEQ ID NO:31) and C3b (SEQ ID NO:32). C3b is in turn converted by thrombin to the product polypeptides iC3b (SEQ ID NO:33) and C3f (SEQ ID NO:36). In one embodiment, the markers of the invention include polypeptides which are N-terminal fragments of iC3b, such as polypeptides having the sequence set forth in SEQ ID NOS:34 and 35. The markers of the invention may also include full length C3f (SEQ ID NO:36) and fragments thereof, including polypeptides having the sequence set forth as (SEQ ID NO:37). In yet another embodiment, the markers of the invention include polypeptides derived from thymosin beta 1 (SEQ ID NO:38), thymosin beta 3 (SEQ ID NO:39), thymosin beta 4 (SEQ ID NO:40), or thymosin beta 6 (SEQ ID NO:41), and fragments thereof, including polypeptides having the sequence set forth as SEQ ID NOS:42 and 43. The invention also provides isolated nucleic acid molecules which encode the amino acid sequences set forth herein.

TABLE 1

| Gene Name | Exemplary Sequence | SEQ ID NO (AAs) |
|---|---|---|
| Fibrinogen (alpha chain) | GenBank Accession No. P02671 | 1 |
| Fibrinogen (beta chain) | GenBank Accession No. P02675 | 2 |
| Fibrinopeptide A | H-ADSGEGDFLAEGGGVR-OH | 3 |
| Fibrinopeptide A (wherein serine residue has been converted into dehydroalanine) | H-AD(dehydroA)GEGDFLAEGGGVR-OH | 4 |
| a fragment derived from an N-terminal truncation of fibrinopeptide A | H-DSGEGDFLAEGGGVR-OH; | 5 |
| | H-DSGEGDFLAEGGGV-OH; | 6 |
| | H-SGEGDFLAEGGGVR-OH; | 7 |
| | H-SGEGDFLAEGGGV-OH; | 8 |
| | H-GEGDFLAEGGGVR-OH; | 9 |
| | H-GEGDFLAEGGGV-OH; | 10 |
| | H-EGDFLAEGGGVR-OH; | 11 |
| | H-EGDFLAEGGGV-OH; | 12 |
| | H-GDFLAEGGGVR-OH; | 13 |
| | H-GDFLAEGGGV-OH; | 14 |
| | H-DFLAEGGGVR-OH; | 15 |
| | H-DFLAEGGGV-OH; | 16 |
| | H-FLAEGGGVR-OH; | 17 |
| | H-FLAEGGGV-OH; | 18 |

TABLE 1-continued

| Gene Name | Exemplary Sequence | SEQ ID NO (AAs) |
|---|---|---|
| | H-LAEGGGV-OH; | 19 |
| | H-AEGGGV-OH; | 20 |
| | H-EGGGV-OH. | 21 |
| Phosphoserine-containing fibrinopeptide A | H-ADS*GEGDFLAEGGGVR-OH (S* = phosphoserine) | 22 |
| Phosphoserine-containing fibrinopeptide A fragments derived from an N-terminal truncation thereof | H-DS*GEGDFLAEGGGVR-OH; | 23 |
| | H-DS*GEGDFLAEGGGV-OH; | 24 |
| | H-S*GEGDFLAEGGGVR-OH; | 25 |
| | H-S*GEGDFLAEGGGV-OH (S* = phosphoserine) | 26 |
| fibrinopeptide B | QGVNDNEEGF FSAR | 27 |
| des-arginine-L-pyroglutamic acid fibrinopeptide B | pyr-EGVNDNEEGFFSA-OH | 28 |
| internal fragment of the fibrinogen alpha chain | H-DEAGSEADHEGTHST-OH | 29 |
| Complement C3 | GenBank Accession No. P01024 | 30 |
| C3a | SVQLTEKRM DKVGKYPKEL RKCCEDGMRE NPMRFSCQRR TRFISLGEAC KKVFLDCCNY ITELRRQHAR ASHLGLAR | 31 |
| C3b | See Sequence Listing | 32 |
| iC3b | See Sequence Listing | 33 |
| N-terminal fragments of iC3b | H-SEETKENEGFTVTAEG-OH; | 34 |
| | H-EETKENEGFTVTAEG-OH | 35 |
| C3f | H-SSKITHRIHWESASLLR-OH | 36 |
| C3f fragment | H-HWESASLL-OH | 37 |
| Thymosin beta 1 | SDKPDMAEME KFDKSKLKKT ETQEKNPLPS KETIEQEKQA GES | 38 |
| Thymosin beta 3 | SDKPDMAEIE KFDKPKLKKT ETQEKNPLPS KETIEQEKQA GES | 39 |
| Thymosin beta 4 | GenBank Accession No. P01253 | 40 |
| Thymosin beta 6 | SDKSDMAEIE KFDKSKLKKT ETQEKNPLPS KETIEQEKQA GES | 41 |
| Fragments of thymosin | H-TQEKNPLPSKETIEQEKQAGES-OH; | 42 |
| | Pyr-EKNPLPSKETIEQEKQAGES-OH | 43 |

TABLE 2

| Gene Name | Exemplary Sequence | SEQ ID NO (AAs) |
|---|---|---|
| Fibrinogen (alpha chain) | GenBank Accession No. P02671 | 1 |
| Fibrinogen (beta chain) | GenBank Accession No. P02675 | 2 |
| Fibrinopeptide A | H-ADSGEGDFLAEGGGVR-OH | 3 |
| Fibrinopeptide A (wherein serine residue has been converted into dehydroalanine) | H-AD(dehydroA)GEGDFLAEGGGVR-OH | 4 |
| a fragment derived from an N-terminal truncation of fibrinopeptide A | H-DSGEGDFLAEGGGVR-OH; | 5 |
| | H-DSGEGDFLAEGGGV-OH; | 6 |
| | H-SGEGDFLAEGGGVR-OH; | 7 |
| | H-SGEGDFLAEGGGV-OH; | 8 |
| | H-GEGDFLAEGGGVR-OH; | 9 |
| | H-GEGDFLAEGGGV-OH; | 10 |
| | H-EGDFLAEGGGVR-OH; | 11 |
| | H-EGDFLAEGGGV-OH; | 12 |
| | H-GDFLAEGGGVR-OH; | 13 |
| | H-GDFLAEGGGV-OH; | 14 |
| | H-DFLAEGGGVR-OH; | 15 |
| | H-DFLAEGGGV-OH; | 16 |
| | H-FLAEGGGVR-OH; | 17 |
| | H-FLAEGGGV-OH; | 18 |
| | H-LAEGGGV-OH; | 19 |
| | H-AEGGGV-OH; | 20 |
| | H-EGGGV-OH | 21 |
| Phosphoserine-containing fibrinopeptide A | H-ADS*GEGDFLAEGGGVR-OH (S* = phosphoserine) | 22 |
| Phosphoserine-containing fibrinopeptide A fragments derived from an N-terminal truncation thereof | H-DS*GEGDFLAEGGGVR-OH; | 23 |
| | H-DS*GEGDFLAEGGGV-OH; | 24 |
| | H-S*GEGDFLAEGGGVR-OH; | 25 |
| | H-S*GEGDFLAEGGGV-OH (S* = phosphoserine) | 26 |
| fibrinopeptide B | QGVNDNEEGF FSAR | 27 |
| des-arginine-L-pyroglutamic acid fibrinopeptide B | Pyr-EGVNDNEEGFFSA-OH | 28 |
| internal fragment of the fibrinogen alpha chain | H-DEAGSEADHEGTHST-OH | 29 |
| Complement C3 | GenBank Accession No. P01024 | 30 |
| C3a | SVQLTEKRM DKVGKYPKEL RKCCEDGMRE NPMRFSCQRR TRFISLGEAC KKVFLDCCNY ITELRRQHAR ASHLGLAR | 31 |
| C3b | See Sequence Listing | 32 |

TABLE 2-continued

| Gene Name | Exemplary Sequence | SEQ ID NO (AAs) |
|---|---|---|
| C3f | H-SSKITHRIHWESASLLR-OH | 36 |
| C3f fragment | H-HWESASLL-OH | 37 |

TABLE 3

| Gene Name | Exemplary Sequence | SEQ ID NO (AAs) |
|---|---|---|
| iC3b | See Sequence Listing | 33 |
| N-terminal fragments of iC3b | H-SEETKENEGFTVTAEG-OH; | 34 |
| | H-EETKENEGFTVTAEG-OH | 35 |
| Thymosin beta 1 | SDKPDMAEME KFDKSKLKKT ETQEKNPLPS KETIEQEKQA GES | 38 |
| Thymosin beta 3 | SDKPDMAEIE KFDKPKLKKT ETQEKNPLPS KETIEQEKQA GES | 39 |
| Thymosin beta 4 | GenBank Accession No. P01253 | 40 |
| Thymosin beta 6 | SDKSDMAEIE KFDKSKLKKT ETQEKNPLPS KETIEQEKQA GES | 41 |
| Fragments of thymosin | H-TQEKNPLPSKETIEQEKQAGES-OH; | 42 |
| | Pyr-EKNPLPSKETIEQEKQAGES-OH | 43 |

Thus, in one embodiment, a marker polypeptide of the invention is fibrinogen or a fragment thereof, such as fibrinopeptide A or a fragment thereof. The fragment of fibrinopeptide A can be, for example, a fragment derived from an N-terminal truncation of fibrinopeptide A. For example, the marker polypeptides of the invention can include one or more polypeptides having the sequences ADSGEGDFLAEGGGVR (fibrinopeptide A) (SEQ ID NO:3); DSGEGDFLAEGGGVR (SEQ ID NO:5); DSGEGDFLAEGGGV (SEQ ID NO:6); SGEGDFLAEGGGVR (SEQ ID NO:7); SGEGDFLAEGGGV (SEQ ID NO:8); GEGDFLAEGGGVR (SEQ ID NO:9); GEGDFLAEGGGV (SEQ ID NO:10); EGDFLAEGGGVR (SEQ ID NO:11); EGDFLAEGGGV (SEQ ID NO:12); GDFLAEGGGVR (SEQ ID NO:13); GDFLAEGGGV (SEQ ID NO:14); DFLAEGGGVR (SEQ ID NO:15); DFLAEGGGV (SEQ ID NO:16); FLAEGGGVR (SEQ ID NO:17); FLAEGGGV (SEQ ID NO:18); LAEGGGV (SEQ ID NO:19); AEGGGV (SEQ ID NO:20); and EGGGV (SEQ ID NO:21). Fibrinopeptide A and fragments thereof wherein the serine residue has been phosphorylated or converted into dehydroalanine are also included. Such peptides include AD(dehydroA)GEGDFLAEGGGVR (SEQ ID NO:4); ADS*GEGDFLAEGGGVR (phosphorylated fibrinopeptide A) (SEQ ID NO:22); DS*GEGDFLAEGGGVR (SEQ ID NO:23); DS*GEGDFLAEGGGV (SEQ ID NO:24); S*GEGDFLAEGGGVR (SEQ ID NO:25); and S*GEGDFLAEGGGV (SEQ ID NO:26), where "dehydroA" represents dehydroalanine and "S*" represents phosphoserine.

The marker polypeptides of the invention also include the fibrinogen β-chain or a fragment thereof, such as fibrinopeptide B or a fragment thereof. In another embodiment, the marker polypeptides of the invention include fibrinopeptide B and derivatives and fragments thereof, including des-arginine-L-pyroglutamic acid fibrinopeptide B, pyr-EGVNDNEEGFFSA (SEQ ID NO:28). The N-terminal Gln has been cyclized to form a pyroglutamate. It will be appreciated that pyr-E in the sequences of the invention represents pyroglutamate.

In a further aspect, the marker polypeptides of the invention include an internal fragment of the fibrinogen α-chain, such as a peptide having the sequence DEAGSEADHEGTHST (SEQ ID NO:29).

The marker polypeptides of the invention also include peptides derived from Complement component 3 (Complement C3). Complement C3 is converted by the enzyme C3 convertase to two protein products, C3a and C3b. C3b is in turn converted by thrombin to the product peptides iC3b and C3f. In one embodiment, the biomarkers of the invention include peptides which are N-terminal fragments of iC3b, such as peptides having the sequence SEETKENEGFTVTAEG (SEQ ID NO:34) or EETKENEGFTVTAEG (SEQ ID NO:35). The biomarkers of the invention also include full length C3f, having the amino acid sequence SSKITHRIHWESASLLR (SEQ ID NO:36), and fragments thereof, including peptides having the sequence HWESASLL (SEQ ID NO:37).

In yet another embodiment, the marker polypeptides of the invention include peptides derived from thymosin beta 1, thymosin beta 3, thymosin beta 4, or thymosin beta 6, and fragments thereof, including peptides having the sequence TQEKNPLPSKETIEQEKQAGES (SEQ ID NO:42) or the sequence pyr-EKNPLPSKETIEQEKQAGES (SEQ ID NO:43). It will be appreciated that pyr-E in the sequences of the invention represents pyroglutamate.

Unless otherwise indicated, the marker polypeptides of the invention have free N- and C-termini. This is shown in Tables 1 to 3 by the N-terminal "H-", which indicates a free amino group at the N-termninus, and the C-terminal "—OH", which indicates a free carboxyl group at the C-terminus.

In another embodiment, the present invention provides isolated polypeptides which are fragments of fibrinogen, fibrinogen α-chain, fibrinopeptide A, fibrinogen β-chain, fibrinopeptide B, C3a, C3b, iC3b, C3f, thymosin beta 1, thymosin beta 3, thymosin beta 4, thymosin beta 6 or analogues thereof. The isolated polypeptides of the invention include polypeptides having an amino acid sequence selected from the group consisting of ADSGEGDFLAE-GGGVR (fibrinopeptide A) (SEQ ID NO:3); DSGEGD-FLAEGGGVR (SEQ ID NO:5); DSGEGDFLAEGGGV (SEQ ID NO:6); SGEGDFLAEGGGVR (SEQ ID NO:7); SGEGDFLAEGGGV (SEQ ID NO:8); GEGDFLAE-GGGVR (SEQ ID NO:9); GEGDFLAEGGGV (SEQ ID NO:10); EGDFLAEGGGVR (SEQ ID NO:11); EGDFLAE-GGGV (SEQ ID NO:12); GDFLAEGGGVR (SEQ ID NO:13); GDFLAEGGGV (SEQ ID NO:14); DFLAE-GGGVR (SEQ ID NO:15); DFLAEGGGV (SEQ ID NO:16); FLAEGGGVR (SEQ ID NO:17); FLAEGGGV (SEQ ID NO:18); LAEGGGV (SEQ ID NO:19); AEGGGV (SEQ ID NO:20); EGGGV (SEQ ID NO:21); D(dehydroA) GEGDFLAEGGGVR (SEQ ID NO:4); ADS*GEGDFLAEGGGVR (phosphorylated fibrinopeptide A) (SEQ ID NO:22); DS*GEGDFLAEGGGVR (SEQ ID NO:23); DS*GEGDFLAEGGGV (SEQ ID NO:24); S*GEGDFLAEGGGVR (SEQ ID NO:25); S*GEGDFLAEGGGV (SEQ ID NO:26); pyr-EGVND-NEEGFFSA (SEQ ID NO:28); DEAGSEADHEGTHST (SEQ ID NO:29); SEETKENEGFTVTAEG (SEQ ID NO:34); EETKENEGFTVTAEG (SEQ ID NO:35); SSKITHRIHWESASLLR (SEQ ID NO:36); HWESASLL (SEQ ID NO:37); TQEKNPLPSKETIEQEKQAGES (SEQ ID NO:42) and pyr-EKNPLPSKETIEQEKQAGES (SEQ ID NO:43).

The invention also provides isolated nucleic acid molecules which encode an amino acid sequence set forth herein.

In another embodiment, the invention relates to antibodies that bind to and/or can detect a polypeptide of the invention. The antibodies can be polyclonal antibodies or monoclonal antibodies, humanized or chimeric antibodies or fragments thereof.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The "abundance" of a polypeptide marker in a sample is the amount of the marker in the sample, as determined by quantitative analysis. The abundance can be expressed as the absolute amount of the marker polypeptide within the sample, or as a relative amount, such as amount of the polypeptide per unit mass of the sample or the concentration of the polypeptide within the sample. The abundance of the polypeptide in the sample can depend upon a number of factors, such as the level of expression of the polypeptide within the tissue sampled, the extent of transport of the polypeptide from its source to the tissue sampled and the extent of metabolism or processing of a parent protein to produce the polypeptide.

An "analogue" of a reference polypeptide is a polypeptide having substantial identity to the reference polypeptide. For example, an analogue can exhibit 70%, 75%, 80%, 85%, 90% or 95% identity to the reference polypeptide. The analogue can also be a truncated polypeptide resulting from C- and/or N-terminal truncation of the reference polypeptide. An analogue can also have one or more amino acid substitutions compared to the reference polypeptide, such as the substitution of one or more residues with another naturally occurring L-configuration residue, or a non-natural amino acid residue, such as a D-configuration residue or a D- or L-configuration residue bearing a side chain which is different from the side chains of the twenty naturally-occurring L-amino acids. In one embodiment, the analogue results from conservative substitution of one or more residues in the reference polypeptide. The term "conservative substitution" is known in the art and relates to the substitution of an amino acid residue with a residue bearing a side chain of similar properties. In a preferred embodiment, an analogue of a reference polypeptide is immunologically cross-reactive with the reference polypeptide, that is, antibodies raised to the analogue are able to bind to and/or detect the reference polypeptide.

A "marker", as this term is used herein, is a polypeptide whose altered abundance in a tissue, cell or bodily fluid compared to its abundance in normal or healthy tissue, cell or bodily fluid is associated with a disease state, such as endometriosis. A "marker nucleic acid" is a nucleic acid (e.g., mRNA, cDNA) which encodes a marker of the invention. Such marker nucleic acids include DNA (e.g., cDNA) encoding the entire or a partial sequence of any of the SEQ ID NO (AA) or the complement of such a sequence. The marker nucleic acids also include RNA corresponding to the entire or a partial sequence of any marker nucleic acid sequence or the complement of such a sequence, wherein all thymidine residues are replaced with uridine residues.

The term "probe" refers to any molecule which is capable of selectively binding to a specifically intended target molecule, for example, a polynucleotide, a polynucleotide transcript or a polypeptide. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, a "patient sample" or "bodily fluid" can be any bodily fluid in which differences in the amount of at least one marker of the invention is indicative of the presence of endometriosis. Suitable bodily fluids include blood, a blood fraction, urine, saliva, tears, and cerebrospinal fluid. In a preferred embodiment, the bodily fluid is blood or a fraction thereof, such as serum or plasma. More preferably, the bodily fluid is serum. An "endometrial-associated fluid" is a fluid which, when in the body of a patient, contacts or passes through the endometrium or into which cells, nucleic acids or proteins are shed from endometrial cells. Exemplary endometrial-associated body fluids include peritoneal fluid, which is a fluid obtained from the peritoneal cavity, the resulting fluids obtained from a PAP smear procedure, gynecological fluids, and fluids collected by vaginal rinsing.

The term "normal abundance" of a marker is the abundance of the marker in a particular sample, such as blood serum, which is indicative of the absence of endometriosis. For example, the normal abundance of a marker is the abundance found in a sample from a control subject not afflicted with endometriosis. Preferably, the normal abundance is an average value or a range of values found by analysis of samples derived from a plurality of control subjects not afflicted with endometriosis.

The terms "significantly greater abundance" and "over-abundance" of a marker refers to an amount of the marker in a test sample that is greater than the normal abundance of the marker by an amount equal to at least the standard error of the assay employed to determine abundance, and is preferably at least twice, the normal abundance of the marker.

The terms "significantly lower abundance" and "under-abundance" of a marker refer to an amount of the marker in a test sample that is that is less than the normal abundance of the marker by an amount equal to at least the standard error of the assay employed to determine abundance, and is preferably 50% or less of the normal abundance of the marker.

The term "altered abundance" refers to a significantly greater abundance or a significantly lower abundance when compared to the normal abundance.

When comparing the abundance of a marker in a subject to the normal abundance, the comparison is made using like samples. For example, the abundance of a given marker in a serum sample derived from a subject is compared to the normal abundance of the marker in serum. Thus, a marker which is over-abundant or under-abundant in the serum of a subject has an altered abundance relative to the normal abundance in serum.

As used herein, a "patient," "subject" or "female subject" can be any female mamimal, and is preferably a human female. More preferably, the subject is a human female of child-bearing age, i.e., a post-pubescent human female who has not yet entered menopause. The woman may be selected by a physician for evaluation by the method of the invention on the basis of the presence of one or more symptoms of endometriosis, such as abdominal or pelvic pain, irregular menstruation, or infertility.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A chemical entity, such as a protein, polypeptide or antibody, is "isolated" if a composition comprising the entity is substantially free of other macromolecules, such as other proteins. A chemical entity is "purified" in a composition in which the entity is present in substantially greater relative concentration than it exists in its natural state, for example in a body fluid of a subject. Preferably the chemical entity comprises at least 80%, more preferably at least 90%, and even more preferably at least 95% by weight of the macromolecular species present in the composition. Most preferably, the chemical entity is purified to homogeneity, i.e., other macromolecular species are not significantly detectable using standard techniques, such as polyacrylamide gel electrophoresis and high performance liquid chromatography.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Homologous" as used herein, refers to amino acid sequence similarity between regions of two different polypeptide sequences. When an amino acid residue position in both regions is occupied by the same amino acid residue, then the regions are homologous at that position. A first region is homologous to a second region if at least one amino acid residue position of each region is occupied by the same residue. Homology between two regions is expressed in terms of the proportion of amino acid residue positions of the two regions that are occupied by the same amino acid residue. Preferably, the first region comprises a first portion and the second region comprises a second portion, whereby, at least about 50%, and preferably at least about 75%, at least about 90%, or at least about 95% of the amino acid residue positions of each of the portions are occupied by the same amino acid residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

The term "synthetic standard" refers to a synthetic or recombinant polypeptide which is structurally equivalent to one of the marker polypeptides of the invention. The term "internal standard" refers to a compound which is chemically and structurally similar to a marker polypeptide, but which differs from the marker polypeptide in mass.

Endometriosis is "inhibited" if at least one symptom of the disease is alleviated, terminated, slowed, or prevented. As used herein, endometriosis is also "inhibited" if recurrence or progression of the disease is reduced, slowed, delayed, or prevented.

A kit is any manufacture (e.g. a package or container) comprising at least one reagent, e.g. a probe, an antibody, a synthetic standard or an internal standard, for specifically determining the abundance of a marker of the invention. The kit may be promoted, distributed, or sold as a unit for performing the methods of the present invention.

"Polypeptides of the invention" encompass marker polypeptides, such as the polypeptides set forth in Table 1 and their fragments; variant marker polypeptides, such as polypeptides which are homologous to the polypeptides set forth in Table 1, for example, polypeptides which can be used as internal standards, and their fragments; polypeptides and polypeptides comprising an at least 7, 10 or 15 amino acid segment of a marker or variant marker polypeptide; and fusion proteins comprising a marker or variant marker polypeptide, or an at least 7, 10 or 15 amino acid segment of a marker or variant marker polypeptide.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

Description

The present invention is based, in part, on newly identified markers which are over- or under-abundant in samples, such as blood serum, from patients who have endometriosis as compared to unaffected control samples, e.g., serum samples from control subjects that do not have endometriosis. The altered abundance of one or more of these markers in a patient sample is herein correlated with the endometriosis. An altered abundance of some of these markers is also correlated with the stage and clinical outcome of the patient. The invention provides compositions, kits, and methods for assessing the stage of the endometriosis, as well as for treating patients afflicted with endometriosis.

The compositions, kits, and methods of the invention have the following uses, among others:

1) assessing whether a patient is afflicted with endometriosis;
2) assessing the stage of endometriosis in a human patient;
3) predicting the clinical outcome of a patient diagnosed with endometriosis;
4) assessing the nature of endometriosis in a patient;
5) making antibodies, antibody fragments or antibody derivatives that are useful for assessing whether a patient is afflicted with endometriosis;
6) assessing the efficacy of one or more test compounds for inhibiting endometriosis in a patient;
7) assessing the efficacy of a therapy for inhibiting endometriosis in a patient;
8) monitoring the progression of endometriosis in a patient; and
9) selecting a composition or therapy for inhibiting endometriosis in a patient.

The invention thus includes a method of assessing whether a patient is afflicted with endometriosis. This method comprises comparing the abundance of a marker of the invention (listed in Table 1) in a patient sample and the normal abundance of the marker. An altered abundance of the marker in the patient sample as compared to the normal abundance is an indication that the patient is afflicted with endometriosis.

The invention further includes polypeptides comprising the entirety, or a segment of any of the sequences of SEQ ID NO (AAs) and homologues thereof. Gene delivery vehicles, host cells and compositions (all described herein) containing nucleic acids encoding the polypeptides of the invention are also included.

As described herein, endometriosis in a patient is associated with an altered abundance of one or more markers of the invention in a sample or tissue obtained from the patient.

Any marker or combination of markers of the invention, as well as any known markers in combination with the markers of the invention, may be used in the compositions, kits, and methods of the present invention. In general, it is preferable to use markers for which the difference between the abundance of the marker in a sample from a patient having endometriosis and the normal abundance of the same marker is as great as possible. Although this difference can be as small as the limit of detection of the method for assessing abundance of the marker, it is preferred that the difference be at least greater than the standard error of the assessment method, and preferably a difference of at least 2-, 3-, 4-, 5-, 6-, 7-, 8-, 9-, or 10-fold or greater than the nor abundance of the same marker.

It will be appreciated that a variety of patient samples may be used in the methods of the present invention. In these embodiments, the abundance of the marker can be assessed by assessing the amount (e.g. absolute amount or concentration) of the marker in the patient sample, e.g., a bodily fluid, such as a serum sample. The bodily fluid can be obtained from the subject using any available method, which may be selected on the basis of the amount of fluid required. In certain cases, a collected blood sample may be used in a variety of tests and only a portion or aliquot of the sample drawn will be required for use in the methods described herein. The amount of the marker(s) of the invention can be determined in whole blood or in a fraction of the blood. Preferably, the amount of marker is determined for a cell-free fraction of the blood, such as the plasma or the serum. It is particularly preferred to determine the amount of marker(s) in the serum. In embodiments in which only a fraction of the blood is used in the analysis, the method also includes the steps of separating the desired blood fraction from the whole blood acquired from the subject. This separation of blood fractions can be achieved using methods which are well-known in the art.

The bodily fluid may be further processed, as is known in the art, prior to the measurement of the marker. For example, the fluid can be processed to remove a particular protein, such as serum albumin, a set of proteins, or cells or cell components which are present in the fluid and which may interfere with the analysis. The processing can include steps such as precipitation, chromatography, centrifugation, ultrafiltration and dialysis.

The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

In one embodiment the abundance of the marker(s) of the invention in the sample is determined using chromatography, such as liquid chromatography or gas chromatography, with a suitable detection system. In one embodiment, the chromatographic step separates the bodily fluid into fractions, and at least one of the fractions comprises the marker polypeptide. The fraction comprising the marker can be identified using, for example, mass spectrometry, and the amount of marker present can be determined using methods which are well known in the art, for example, by comparing the ion current generated in the mass spectrometer for the marker to that generated by an internal standard of known concentration.

In another embodiment, the abundance of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

Because the compositions, kits, and methods of the invention rely on detection of a difference in the abundance of one or more markers of the invention, it is preferable that the abundance of the marker is significantly greater than the minimum detection limit of the method used to assess abundance.

It is understood that by routine screening of additional patient samples using one or more of the markers of the invention, it will be realized that certain of the markers are associated with endometriosis of various stages based on a weighted point system. The number, size, and location of endometrial implants, plaques, endometriomas, and/or adhesions are considered. According to the American Society for Reproductive Medicine revised classification of endometriosis, Stage I (minimal): 1–5; stage II (mild): 6–15; stage III (moderate): 16–40; stage IV (severe): >40 (Revised ASRM classification. *Fertil Steri* 1997; 67:819.) In addition, as a greater number of patient samples are assessed for expression of the markers of the invention and the outcomes of the individual patients from whom the samples were obtained are correlated, it will also be confirmed that altered abundance of certain of the markers of the invention is strongly correlated with endometriosis and other endometriosis-related diseases or conditions. The compositions, kits, and methods of the invention are thus useful for characterizing the stage, and nature of endometriosis in patients.

When the compositions, kits, and methods of the invention are used for characterizing the stage and nature of endometriosis in a patient, it is preferred that the marker or panel of markers of the invention is selected such that a positive result is obtained in at least about 20%, and preferably at least about 40%, 60%, or 80%, and more preferably in substantially all patients afflicted with endometriosis of the corresponding stage and nature.

When a plurality of markers of the invention are used in the compositions, kits, and methods of the invention, the abundance of each marker in a patient sample can be compared with the normal abundance of each of the plurality of markers in normal samples of the same type, either in a single reaction mixture (i.e. using reagents, such as different fluorescent probes, for each marker) or in individual reaction mixtures corresponding to one or more of the markers. In one embodiment, a significantly increased abundance of more than one of the plurality of markers in the sample, relative to the corresponding normal levels, is an indication that the patient is afflicted with endometriosis. In another embodiment, a significantly lowered abundance of more than one of the plurality of markers in the sample, relative to the corresponding normal levels, is an indication that the patient is afflicted with endometriosis. In another embodiment, a significantly lowered abundance of a first marker in the sample and a significantly increased abundance of a second marker, relative to the corresponding normal levels, is an indication that the patient is afflicted with endometriosis. When a plurality of markers is used, it is preferred that 2, 3, 4, 5, 6, 7, 8, 9, 10, 12, 15, 20, 30, or 50 or more individual markers be used. In general, it is preferable to use the fewest markers required to provide a test with the desired characteristics.

In one preferred embodiment, a marker polypeptide derived from each of two or more parent proteins can be monitored. For example, one set of marker polypeptides which can be monitored includes H-ADSGEGDFLAE-GGGVR-OH (SEQ ID NO:22); Pyr-EGVNDNEEGFFSA-OH (SEQ ID NO:28); H-HWESASLL-OH (SEQ ID NO:37); H-EETKENEGFTVTAEG-OH (SEQ ID NO:35); and H-TQEKNPLPSKETIEQEKQAGES-OH (SEQ ID NO:42).

Markers associated with the presence of endometriosis have been described, including those disclosed in U.S. Pat. Nos. 5,843,673; 5,618,689 and 6,525,187 and published PCT applications WO 00/43789; WO 99/55902; WO 00/63675; WO 96/20404; WO 99/63116; WO 01/62959; WO 95/13821; and WO 00/47739, the contents of all of which are incorporated herein by reference. These markers are not, of course, included among the markers of the invention, although they may be used together with one or more markers of the invention in a panel of markers, for example.

It is recognized that the compositions, kits, and methods of the invention will be of particular utility to patients having an enhanced risk of developing endometriosis and their medical advisors. Patients recognized as having an enhanced risk of developing endometriosis include, for example, patients having a familial history of endometriosis, patients identified as having altered abundance of a marker of the invention, and patients with a history of pelvic pain, abdominal pain, irregular menstruation and/or infertility.

The normal abundance of a marker in a particular type of biological sample (i.e., in samples from patients that do not have endometriosis) can be assessed in a variety of ways. In one embodiment, as further information becomes available as a result of routine performance of the methods described herein, population-average values for normal abundance of the markers of the invention may be used. In other embodiments, the normal abundance of a marker may be determined by assessing abundance of the marker in a patient sample obtained from a non-endometriosis-afflicted patient, from a patient sample obtained from a patient before the suspected onset of endometriosis in the patient, from archived patient samples, and the like.

The invention includes compositions, kits, and methods for assessing the presence of endometriosis in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of endometriosis (e.g. in a sample such as a patient sample). The kit comprises a plurality of reagents, each of which is capable of binding specifically with a marker polypeptide. Suitable reagents for binding with a marker polypeptide include antibodies, antibody derivatives, antibody fragments, and the like.

The kit of the invention may optionally comprise additional components useful for performing the methods of the invention. By way of example, the kit may comprise fluids (e.g. SSC buffer) suitable for binding an antibody with a polypeptide with which it specifically binds, one or more sample compartments, instructional material, such as a instruction manual, which describes performance of a method of the invention, and a positive and negative control.

The invention also includes a method of making an isolated hybridoma which produces an antibody useful for assessing whether a patient is afflicted with endometriosis. In this method, a protein or polypeptide comprising the entirety or a segment of a marker polypeptide is synthesized or isolated (e.g. by purification from a cell in which it is expressed or by transcription and translation of a nucleic acid encoding the protein or polypeptide in vivo or in vitro using known methods). A vertebrate, preferably a mammal such as a mouse, rat, rabbit, or sheep, is immunized using the protein or polypeptide. The vertebrate may optionally (and preferably) be immunized at least one additional time with the protein or polypeptide, so that the vertebrate exhibits a robust immune response to the protein or polypeptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting endometriosis. As described above, differences in the abundance of the markers of the invention correlate with endometriosis. Although it is recognized that changes in the levels of certain of the markers of the invention likely result from endometriosis, it is likewise recognized that changes in the abundance of other of the markers of the invention may be directly or indirectly associated with the induction, maintenance, and/or promotion of endometriosis. Thus, compounds which inhibit endometriosis in a patient will cause the abundance of one or more of the markers of the invention to change to a level nearer the normal abundance level for that marker.

This method thus comprises comparing abundance of a marker in a first patient sample and maintained in the presence of the test compound and expression of the marker in a second patient sample and maintained in the absence of the test compound. A significantly altered abundance of a marker of the invention in the presence of the test compound is an indication that the test compound inhibits endometriosis. The patient samples may, for example, be aliquots of a single sample of normal endometrial cells obtained from a patient, pooled samples of normal endometrial cells obtained from a patient, cells of a normal endometrial cell line, aliquots of a single sample of endometrial cells obtained from a patient, pooled samples of endometrial cells obtained from a patient, cells of an endometrial cell line, a serum sample, or the like. In one embodiment, the samples include serum from the patient or endometrial cells obtained from a patient and a plurality of compounds known to be effective for inhibiting endometriosis are tested in order to identify the compound which is likely to best inhibit the endometriosis in the patient.

This method may likewise be used to assess the efficacy of a therapy for inhibiting endometriosis in a patient. In this method, the abundance of one or more markers of the invention in a pair of samples (one subjected to the therapy, the other not subjected to the therapy) is assessed. As with the method of assessing the efficacy of test compounds, if the therapy induces a significantly altered abundance (i.e., causes the abundance to approach normal values) of a marker of the invention then the therapy is efficacious for inhibiting endometriosis. As above, if samples from a selected patient are used in this method, then alternative therapies can be assessed in vitro in order to select a therapy most likely to be efficacious for inhibiting endometriosis in the patient.

Various aspects of the invention are described in further detail in the following subsections.

I. Isolated Nucleic Acid Molecules

One aspect of the invention pertains to isolated nucleic acid molecules, including nucleic acids which encode a marker polypeptide or a portion (fragment) thereof. Isolated nucleic acids of the invention also include nucleic acid molecules sufficient for use as hybridization probes to identify these nucleic acid molecules and fragments of these nucleic acid molecules, e.g., those suitable for use as PCR primers for the amplification or mutation of the nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker polypeptide. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker polypeptide. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the polypeptide, such as by measuring levels of a nucleic acid molecule encoding the polypeptide in a sample of cells from a subject, e.g., detecting mRNA levels or determining whether a gene encoding the polypeptide has been mutated or deleted.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a to a nucleic acid encoding a marker polypeptide. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1–6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50–65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded polypeptide, without altering the biological activity of the polypeptide encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker polypeptide that contains changes in amino acid residues that are not essential for activity. Such variant marker polypeptides differ in amino acid sequence from the naturally-occurring marker polypeptides, yet retain biological activity. In one embodiment, such a variant marker polypeptide has an amino acid sequence that is at least about 40% identical, 50%, 60%, 70%, 80%, 90%, 95%, or 98% identical to the amino acid sequence of a marker polypeptide.

An isolated nucleic acid molecule encoding a variant marker polypeptide can be created by introducing one or more nucleotide substitutions, additions or deletions into the nucleotide sequence of marker nucleic acids, such that one or more amino acid residue substitutions, additions, or deletions are introduced into the encoded polypeptide. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded polypeptide can be expressed recombinantly and the activity of the polypeptide can be determined.

II. Isolated Polypeptides and Antibodies

One aspect of the invention pertains to isolated marker polypeptides and biologically active portions thereof, as well as polypeptide fragments suitable for use as immunogens to raise antibodies directed against a marker polypeptide or a fragment thereof. In one embodiment, the native marker polypeptide can be isolated from cells or tissue sources by an appropriate purification scheme using standard polypeptide purification techniques. In another embodiment, a polypeptide comprising the whole or a segment of the marker polypeptide is produced by recombinant DNA techniques. Alternative to recombinant expression, such a polypeptide can be synthesized chemically using standard polypeptide synthesis techniques.

An "isolated" or "purified" polypeptide or biologically active portion thereof is substantially free of cellular material or other contaminating proteins from the cell or tissue source from which the polypeptide is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Thus, polypeptide that is substantially free of cellular material includes preparations of polypeptide having less than about 30%, 20%, 10%, or 5% (by dry weight) of heterologous polypeptide (also referred to herein as a "contaminating polypeptide"). When the polypeptide or biologically active portion thereof is recombinantly produced, it is also preferably substantially free of culture medium, i.e., culture medium represents less than about 20%, 10%, or 5% of the volume of the polypeptide preparation. When the polypeptide is produced by chemical synthesis, it is preferably substantially free of chemical precursors or other chemicals, i.e., it is separated from chemical precursors or other chemicals which are involved in the synthesis of the polypeptide. Accordingly such preparations of the polypeptide have less than about 30%, 20%, 10%, 5% (by dry weight) of chemical precursors or compounds other than the polypeptide of interest.

Preferred marker polypeptides are those having an amino acid sequence of any of the SEQ ID NO (AAs). Other useful polypeptides are substantially identical (e.g., at least about 40%, preferably 50%, 60%, 70%, 80%, 90%, 95%, or 99%) to one of these sequences and retain the functional activity of the corresponding naturally-occurring marker polypeptide yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the BLASTN and BLASTX programs of Altschul, et al. (1990) *J. Mol. Biol.* 215:403–410. BLAST nucleotide searches can be performed with the BLASTN program, score=100, wordlength=12 to obtain nucleotide sequences homologous to a nucleic acid molecules of the invention. BLAST polypeptide searches can be performed with the BLASTP program, score=50, wordlength=3 to obtain amino acid sequences homologous to a polypeptide molecules of the invention. To obtain gapped alignments for comparison purposes, a newer version of the BLAST algorithm called Gapped BLAST can be utilized as described in Altschul et al. (1997) *Nucleic Acids Res.* 25:3389–3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444–2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides polypeptides which can be used as internal standards for the marker polypeptides of the invention, for example, in methods employing mass spectrometry. Such polypeptides include polypeptides expected to behave in the analysis substantially similar to the marker, but that have a mass which is distinct from the marker. Such polypeptides include isotopically-labelled versions of the marker polypeptides, including versions of the marker polypeptides which include one or more deuterium, tritium, $^{15}$N, $^{13}$C, $^{14}$C, $^{32}$P, $^{35}$S or a combination thereof. Other suitable polypeptides for use as internal standards include those differing from the marker polypeptides by a small structural element, for example, the addition or deletion of a methylene (—CH$_2$—) group, a methyl group, or a halogen atom, such as a fluorine, chlorine, bromine or iodine atom. Included are polypeptides which are highly homologous to one of the marker polypeptides, for example, those differing by the identity of one amino acid residue from the marker sequence. Suitable amino acid substitutions include conservative substitutions, including substitutions with homologous amino acid residues, such as substitution of praline with homoproline, substitutions among valine and leucine or isoleucine, and others as can be determined by the skilled artisan.

In another embodiment, the invention relates to chimeric or fusion proteins comprising a marker polypeptide of the invention or a segment thereof. As used herein, a "chimeric protein" or "fusion protein" comprises all or part (preferably a biologically active part) of a marker polypeptide operably linked to a heterologous polypeptide (i.e., a polypeptide other than the marker polypeptide). Within the fusion protein, the term "operably linked" is intended to indicate that the marker polypeptide or segment thereof and the heterologous polypeptide are fused in-frame to each other. The heterologous polypeptide can be fused to the amino-terminus or the carboxyl-terminus of the marker polypeptide or segment.

One useful fusion protein is a GST fusion protein in which a marker polypeptide or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker polypeptide can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker polypeptides. Signal sequences are typically characterized by a core of hydrophobic amino acids which are generally cleaved from the mature protein during secretion in one or more cleavage events. Such signal polypeptides contain processing sites that allow cleavage of the signal sequence from the mature proteins as they pass through the secretory pathway. Thus, the invention pertains to marker polypeptides, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker polypeptide or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

Another aspect of the invention pertains to antibodies directed against a polypeptide of the invention. In preferred embodiments, the antibodies specifically bind a marker polypeptide or a fragment thereof. The terms "antibody" and "antibodies", as used interchangeably herein, refer to immunoglobulin molecules as well as fragments and derivatives thereof that comprise an immunologically active portion of an immunoglobulin molecule, (i.e., such a portion contains an antigen binding site which specifically binds an antigen, such as a marker polypeptide, e.g., an epitope of a marker protein). An antibody which specifically binds to a polypeptide of the invention is an antibody which binds the polypeptide, but does not substantially bind other molecules in a sample, e.g., a biological sample, which naturally contains the polypeptide. Examples of an immunologically active portion of an immunoglobulin molecule include, but are not limited to, single-chain antibodies (scAb), F(ab) and F(ab')$_2$ fragments.

An isolated polypeptide of the invention or a fragment thereof can be used as an immunogen to generate antibodies. The full-length polypeptide can be used or, alternatively, the invention provides antigenic polypeptide fragments for use as immunogens. The antigenic polypeptide of the invention comprises at least 7 (preferably 8, 10, 15, 20, or 30 or more) amino acid residues of the amino acid sequence of one of the proteins of the invention, and encompasses at least one epitope of the protein such that an antibody raised against the polypeptide forms a specific immune complex with the protein. Preferred epitopes encompassed by the antigenic polypeptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker polypeptide or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide or polypeptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a polypeptide of the invention. In such a manner, the resulting antibody compositions have reduced or no binding of human proteins other than a polypeptide of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a polypeptide of the invention.

Particularly preferred polyclonal and monoclonal antibody preparations are ones that contain only antibodies directed against a marker polypeptide or fragment thereof.

Polyclonal antibodies can be prepared by immunizing a suitable subject with a polypeptide of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256: 495–497, the human B cell hybridoma technique (see Kozbor et al., 1983, *Immunol. Today* 4:72), the EBV-hybridoma technique (see Cole et al., pp. 77–96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

The invention also provides recombinant antibodies that specifically bind a polypeptide of the invention. In preferred embodiments, the recombinant antibodies specifically binds a marker polypeptide or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptides. They can be produced by techniques known in the art, for example using methods described in Ladner et. al U.S. Pat. No. 4,946,778 (which is incorporated herein by reference in its entirety); Bird et al., (1988) *Science* 242:423–426; Whitlow et al., (1991) *Methods in Enzymology* 2:1–9; Whitlow et al., (1991) *Methods in Enzymology* 2:97–105; and Huston et al., (1991) *Methods in Enzymology Molecular Design and Modeling: Concepts and Applications* 203:46–88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al, (1993) *Proc. Natl. Acad. Sci. USA* 90:6444–6448; Whitlow et al., (1994) *Protein Eng.* 7:1017–1026 and U.S. Pat. No. 6,121,424.

The antibodies of the invention can be isolated after production (e.g., from the blood or serum of the subject) or synthesis and further purified by well-known techniques. For example, IgG antibodies can be purified using protein A chromatography. Antibodies specific for a polypeptide of the invention can be selected or (e.g., partially purified) or purified by, e.g., affinity chromatography. For example, a recombinantly expressed and purified (or partially purified) polypeptide of the invention is produced as described herein, and covalently or non-covalently coupled to a solid support such as, for example, a chromatography column. The column can then be used to affinity purify antibodies specific for the polypeptides of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired polypeptide of the invention.

An antibody directed against a polypeptide of the invention can be used to isolate the polypeptide by standard techniques, such as affinity chromatography or immunoprecipitation. Moreover, such an antibody can be used to detect the marker polypeptide or fragment thereof (e.g., in a cellular lysate or cell supernatant) in order to evaluate the level and pattern of expression of the marker. The antibodies can also be used diagnostically to monitor polypeptide levels in tissues or body fluids (e.g. in an endometrial-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Accordingly, in one aspect, the invention provides substantially purified antibodies, antibody fragments and derivatives, all of which specifically bind to a polypeptide of the invention and preferably, a marker polypeptide. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a polypeptide of the invention and preferably, a marker polypeptide. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a polypeptide of the invention and preferably, a marker polypeptide. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In one embodiment, the pharmaceutical composition comprises an antibody of the invention, a therapeutic moiety, and a pharmaceutically acceptable carrier.

III. Recombinant Expression Vectors and Host Cells

Another aspect of the invention pertains to vectors, preferably expression vectors, containing a nucleic acid encoding a marker polypeptide (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or polypeptides, including fusion proteins or polypeptides, encoded by nucleic acids as described herein.

The recombinant expression vectors of the invention can be designed for expression of a marker polypeptide or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31–40), pMAL (New England Biolabs, Beverly, Mass.) and pRIT5 (Pharniacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301–315) and pET 11d (Studier et al., p. 60–89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119–128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229–234), pMFa (Kuijan and Herskowitz, 1982, *Cell* 30:933–943), pJRY88 (Schultz et al., 1987, *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156–2165) and the pVL series (Lucklow and Summers, 1989, *Virology* 170:31–39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et aL, supra.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a marker polypeptide or a segment thereof. Accordingly, the invention further provides methods for producing a marker polypeptide or a segment thereof using the host cells of the invention. In one embodiment, the method comprises culturing the host cell of the invention (into which a recombinant expression vector encoding a marker polypeptide or a segment thereof has been introduced) in a suitable medium such that the polypeptide is produced. In another embodiment, the method further comprises isolating the marker polypeptide or a segment thereof from the medium or the host cell.

IV. Pharmaceutical Compositions

The invention also provides methods (also referred to herein as "screening assays") for identifying modulators, i.e., candidate or test compounds or agents (e.g., polypeptides, peptidomimetics, peptoids, small molecules or other drugs) which have a modulatory effect on the abundance of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of polypeptides, but with a novel, non-peptide backbone which are resistant to enzymatic degradation but which nevertheless remain bioactive; see, e.g., Zuckermann et al., 1994, *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to polypeptide libraries, while the other four approaches are applicable to polypeptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412–421), or on beads (Lam, 1991, *Nature* 354:82–84), chips (Fodor, 1993, *Nature* 364:555–556), bacteria and/or spores, (Ladner, U.S. Pat. No. 5,223,409), plasmids (Cull et al., 1992, *Proc Natl Acad Sci USA* 89:1865–1869) or on phage (Scott and Smith, 1990, *Science* 249:386–390; Devlin, 1990, *Science* 249: 404–406; Cwirla et al., 1990, *Proc. Natl. Acad. Sci.* 87:6378–6382; Felici, 1991, *J. Mol. Biol.* 222:301–310; Ladner, supra.).

In one embodiment, the invention provides assays for screening candidate or test compounds which are substrates of a polypeptide encoded by or corresponding to a marker or biologically active portion thereof. In another embodiment, the invention provides assays for screening candidate or test compounds which bind to a polypeptide encoded by or corresponding to a marker or biologically active portion thereof. Determining the ability of the test compound to directly bind to a polypeptide can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker In another aspect, the invention pertains to a combination of two or more of the assays described herein. For example, a modulating agent can be identified using a cell-based or a cell free assay, and the ability of the agent to modulate the activity of a marker polypeptide can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a marker modulating agent) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The pharmaceutical compositions can be included in a container, pack, or dispenser together with instructions for administration.

V. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker polypeptides in order to determine whether an individual is at risk of developing endometriosis. Such assays can be used for prognostic or predictive purposes to thereby prophylactically treat an individual prior to the onset of endometriosis.

Yet another aspect of the invention pertains to monitoring the influence of agents (e.g., drugs or other compounds administered either to inhibit endometriosis or to treat or prevent any other endometriosis-related disease, disorder or condition) on the abundance of a marker of the invention in clinical trials. These and other agents are described in further detail in the following sections.

A. Diagnostic Assays

An exemplary method for detecting the presence, absence or abundance of a marker polypeptide in a biological sample involves obtaining a biological sample (e.g. an endometrial-associated body fluid, blood, blood plasma or serum) from a test subject and contacting the biological sample with a compound or an agent capable of detecting the polypeptide . In vitro techniques for detection of a marker polypeptide include enzyme linked immunosorbent assays (ELISAs), Western blots, immunoprecipitations and immunofluorescence.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay comprises anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' polypeptide molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338–2345 and Szabo et al., 1995, *Curr. Opin. Struct. Biol.* 5:699–705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8): 284–7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1–6):141–8; Hage, D. S., and Tweed, S. A. *J. Chromatogr B Biomed Sci Appl* 1997 Oct 10;699(1–2): 499–525). Gel electrophoresis may also be employed to separate complexed assay components from unbound components (see, e.g., Ausubel et al., ed., *Current Protocols in Molecular Biology*, John Wiley & Sons, New York, 1987–1999). In this technique, polypeptide or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

Alternatively, the abundance can be provided as a relative abundance. To determine a relative abundance of a marker, the abundance of the marker is determined for 10 or more samples of normal (non-endometriosis) samples, preferably 50 or more samples, prior to the determination of the abundance for the sample in question. The mean abundance of each of the markers assayed in the larger number of samples is determined and this is used as a baseline abundance level for the marker. The abundance of the marker determined for the test sample (absolute level of expression) is then divided by the mean abundance value obtained for that marker. This provides a relative abundance.

Preferably, the samples used in the baseline determination will be from blood, serum or plasma. The choice of the sample is dependent on the use of the relative abundance and the ease of obtaining and processing the sample. Using normal abundance as a mean abundance score aids in validating whether the marker assayed is endometriosis specific (versus normal). In addition, as more data is accumulated, the mean expression value can be revised, providing improved relative abundance values based on accumulated data. Abundance data provide a means for grading the severity of the endometriosis state.

In another embodiment of the present invention, a marker polypeptide is detected. A preferred agent for detecting a marker polypeptide of the invention is an antibody capable of binding to the polypeptide or a fragment thereof, preferably an antibody with a detectable label. Antibodies can be polyclonal, or more preferably, monoclonal. An intact antibody, or a fragment or derivative thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a polypeptide that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known polypeptide/antibody detection methods for use in determining the abundance of a marker of the present invention within a given sample.

In one format, antibodies, or antibody fragments or derivatives, can be used in methods such as Western blots or immunofluorescence techniques to detect the expressed polypeptides. In such uses, it is generally preferable to immobilize either the antibody or polypeptides on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, polypeptide isolated from endometrial cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In one embodiment, the abundance of a marker or collection of markers of the invention is determined using mass spectrometric methods. For example, following pretreatment, if any, the sample can be subjected to liquid chromatography/mass spectrometry ("LC/MS"), a method is which the components of the sample are separated by the chromatographic step and then analyzed by mass spectrometry. The method thus provides mass scan data as a fuinction of retention time. Because of the possibility that the analyte of interest will co-elute with another sample component having the same mass, the sample is preferably analyzed using liquid chromatography/mass spectrometry/mass spectrometry ("LC/MS/MS"), a method in which the molecular ions from the first mass spectrometric step are fragmented. Such a method typically provides one or more fragments which is unique to the analyte of interest and can be monitored. The LC/MS/MS method thus provides a means of monitoring a specific analyte without interference from other sample components and is particularly useful when the sample includes a complex mixture of components.

In one embodiment, the mass spectrometer is set to scan over a small mass range which includes the mass of the analyte. In an LC/MS/MS method, the analyte can be determined using Selective Reaction Monitoring ("SRM"). In SRM, the parent mass of the analyte is specified for further fragmentation, and a specific fragment ion is monitored. In a Multiple Reaction Monitoring ("MRM") experiment two or more parent-fragment pairs are monitored.

In a preferred embodiment, a known quantity of internal standard is added to the sample prior analysis of the sample. Preferably, an internal standard is added for each marker polypeptide to be analyzed. The internal standard is preferably added to the sample prior to any processing of the sample. The internal standard is a compound which is closely related structurally to the analyte of interest, but that has a different mass than the analyte. For example, the internal standard should be a compound which behaves essentially identically to the marker during sample preparation, chromatographic separation and ionization in the mass spectrometer. Thus, the internal standard is preferably, a compound which has structural, physical and chemical features which are very close to those of the marker polypeptide. Suitable internal standards for the present marker polypeptides include synthetic polypeptides, such as synthetic, isotopically labeled polypeptides having the same structure, other than the isotopic label, as the marker polypeptide to be analyzed. The internal standard polypeptides can be isotoopically labeled in a suitable manner, as is known in the art, such as labeling with $^2$H (deuterium), $^3$H (tritium), $^{13}$C, $^{33}$S, $^{32}$P, $^{15}$N and $^{17}$O. Preferably, the isotopic label is not a radioisotope. Preferred isotopic labels include $^2$H, $^{13}$C, $^{15}$N and $^{17}$O. The internal standard for a given polypeptide marker can also be a polypeptide which differs structurally from the marker polypeptide in a minor way, such as the addition or subtraction of a methylene group, methyl group, hydroxyl group or halogen atom. For example, the following pairs of amino acid residues can be substituted for each other in preparing an internal standard for a given marker polypeptide: gycine/alanine; valine/leucine; valine/isoleucine; cysteine/homocysteine; asparagine/glutamine; aspartic acid/glutamic acid; serine/threonine; and phenylalanine/tyrosine. Similar substitutions can be made using structurally related non-natural amino acid residues, as is known in the art. Examples of suitable internal standards for use in the present method include, but are not limited to, polypeptides of the formula H-EETKENEGFTV-TAEG-OH ($d_8$-Val) (SEQ ID NO:35) and Pyr-EGLNDNEE-GFFSA-OH (SEQ ID NO:44).

Quantitation of a marker polypeptide of the invention can be accomplished using methods known in the art. For example, for a given marker polypeptide, the synthetic standard can be used to generate a calibration curve. To generate a calibration curve, the synthetic standard is added to blank or surrogate matrix in varying amounts, the samples are pretreated using the desired protocol and then analyzed by LC/MS or LC/MS/MS. The area under the counts per second vs time curve for the ion current (peak area) for the fragment (SIM, SRM) or each of the multiple fragments (MRM) is determined. A calibration curve is constructed in which the concentration ratio of analyte to internal standard is plotted versus peak area ratio. The peak area of the corresponding fragment or fragments of the marker polypeptide is determined and the concentration of the marker polypeptide is found using the calibration curve.

The mass spectrometer to be used in the methods of the invention can be, for example, an ion trap mass spectrometer or a (triple)quadrupole mass spectrometer. Electrospray (atmospheric pressure) ionization is preferably used, but other methods for ionization can also be used, as is known in the art.

The invention also encompasses kits for detecting the presence of a marker polypeptide in a biological sample. Such kits can be used to determine if a subject is suffering from or is at increased risk of developing endometriosis. For example, the kit can comprise a labeled compound or agent capable of detecting one or more marker polypeptides in a biological sample and means for determining the amount of the polypeptide in the sample (e.g., an antibody which binds the polypeptide or fragment thereof.

For antibody-based kits, the kit can comprise, for example: (1) a first antibody (e.g., attached to a solid support) which binds to a marker polypeptide; and, optionally, (2) a second, different antibody which binds to either the polypeptide or the first antibody and is conjugated to a detectable label.

Kits to be used in mass spectrometric methods can include one or more synthetic standards and/or one or more internal standards.

The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

C. Monitoring Clinical Trials

Monitoring the influence of agents (e.g., drug compounds) on the level of expression of a marker of the invention can be applied not only in basic drug screening, but also in clinical trials. For example, the ability of an agent to affect marker abundance can be monitored in clinical trials of subjects receiving treatment for endometriosis. In a preferred embodiment, the present invention provides a method for monitoring the effectiveness of treatment of a subject with an agent (e.g., an agonist, antagonist, peptidomimetic, protein, polypeptide, nucleic acid, small molecule, or other drug candidate) comprising the steps of (i) obtaining a pre-administration sample from a subject prior to administration of the agent; (ii) determining the abundance of one or more selected markers of the invention in the pre-administration sample; (iii) obtaining one or more post-administration samples from the subject; (iv) determining the abundance of the marker(s) in the post-administration samples; (v) comparing the abundance of the marker(s) in the pre-administration sample with the abundance of the marker(s) in the post-administration sample or samples; and (vi) altering the administration of the agent to the subject accordingly. For example, increased abundance of certain marker polypeptide(s) during the course of treatment may indicate ineffective dosage and the desirability of increasing the dosage. Conversely, decreased expression of these marker polypeptide(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as. WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has endometriosis or a pre-disposition to endometriosis, wherein the method comprises the steps of determining the abundance of a marker and, based on the abundance of the marker, determining whether the subject has endometriosis or a pre-disposition to endometriosis and/or recommending a particular treatment for endometriosis or pre-endometriosis condition.

The present invention further provides in an electronic system and/or in a network, a method for determining whether a subject has endometriosis or a pre-disposition to endometriosis associated with a marker wherein the method comprises the steps of determining the abundance of the marker, and based on the abundance of the marker, determining whether the subject has endometriosis or a pre-disposition to endometriosis, and/or recommending a particular treatment for the endometriosis or pre-endometriosis condition. The method may further comprise the step of receiving phenotypic information associated with the subject and/or acquiring from a network phenotypic information associated with the subject.

The present invention also provides in a network, a method for determining whether a subject has endometriosis or a pre-disposition to endometriosis associated with a marker, said method comprising the steps of receiving information associated with the marker, receiving phenotypic information associated with the subject, acquiring information from the network corresponding to the marker and/or endometriosis, and based on one or more of the phenotypic information, the marker, and the acquired information, determining whether the subject has endometriosis or a pre-disposition to endometriosis. The method may further comprise the step of recommending a particular treatment for the endometriosis or pre-endometriosis condition.

The present invention also provides a business method for determining whether a subject has endometriosis or a pre-disposition to endometriosis, said method comprising the steps of receiving information associated with the marker, receiving phenotypic information associated with the subject, acquiring information from the network corresponding to the marker and/or endometriosis, and based on one or more of the phenotypic information, the marker, and the acquired information, determining whether the subject has endometriosis or a pre-disposition to endometriosis. The method may further comprise the step of recommending a particular treatment for the endometriosis or pre-endometriosis condition.

E. Surrogate Markers

The markers of the invention may serve as surrogate markers for one or more disorders or disease states or for conditions leading up to disease states, and in particular, endometriosis. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

VI. Experimental Protocol

A. Identification of the Markers of the Invention

Serum samples were obtained from women with endometriosis confirmed by laparoscopy and from women having no complaints indicative of endometriosis. Samples were also obtained from women diagnosed with polycystic ovarian syndrome (PCOS) and pelvic inflammatory disease (PID). The serum samples were prepared for analysis and analyzed using the following protocol.

50 mL serum was diluted with 100 µL 500 µM aqueous glycine, pH 2.0. The diluted serum was then ultrafiltered using a 10,000 dalton molecular weight cutoff membrane (Millipore; 14,000 RCF maximum) at 3,750 rpm on a swinging bucket for approximately 2.5 hours. The filtrate was transferred to a container for HPLC analysis, which was performed using a Grace Vydac C-8 column (0.21 cm×15 cm; Catalog No. 208TP5215), and an injection volume of 0.1 mL. The column was eluted with a gradient of 95/4.9/0.1 acetonitrile/water/formic acid from 2% to 60% over 30 minutes. The eluate was analyzed by mass spectrometry using a Waters qudrupole-time-of-flight mass spectrometer with a Z-spray source and an mass/charge range of 200 to 2000 daltons. Quantitation of a particular retention time/mass to charge pair was taken as the ion count from the mass spectrometer, which was assumed to be linear with the concentration of the analyte.

Figure 3:
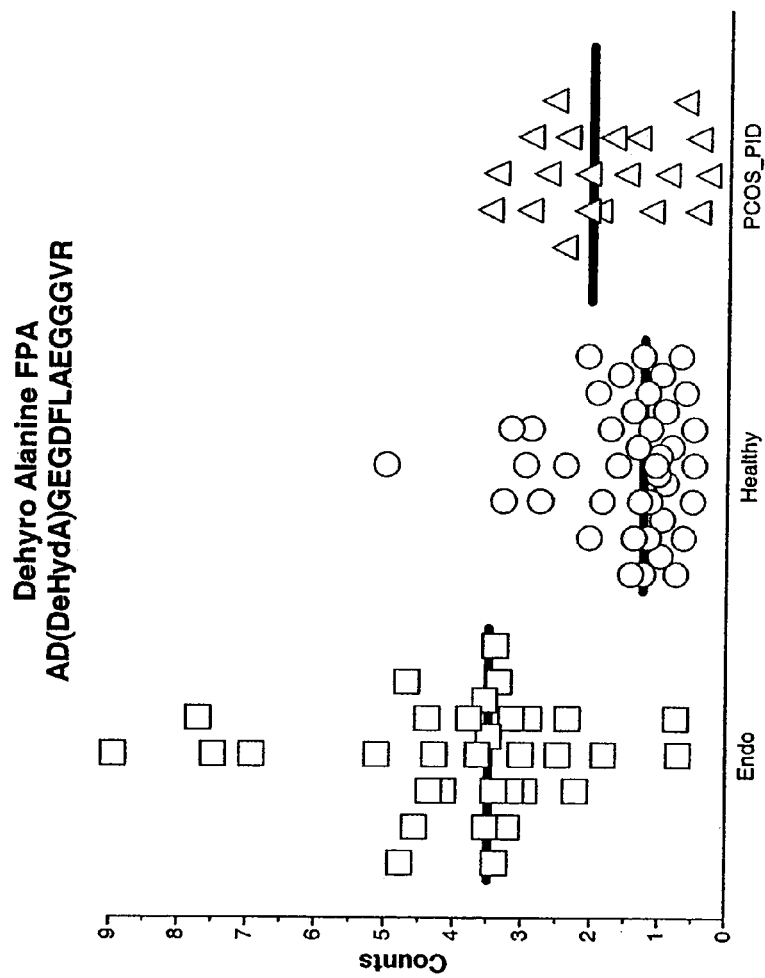
Figure 4:
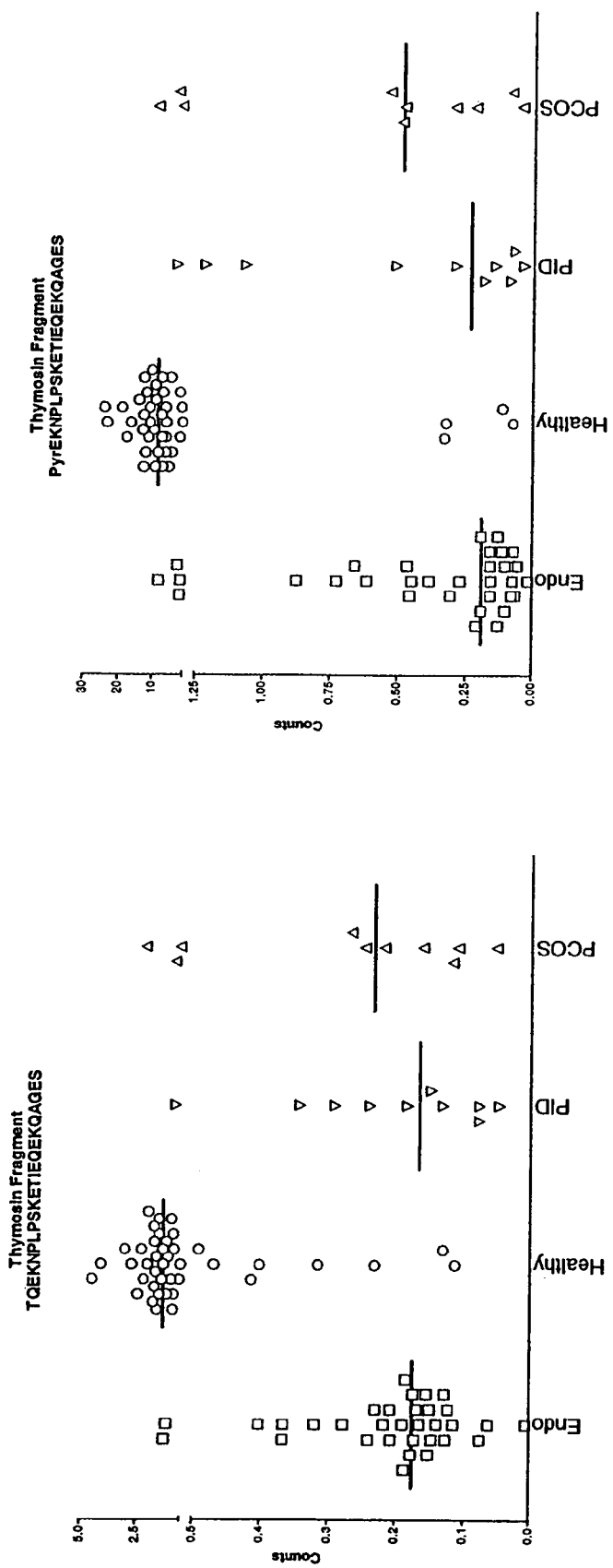
Figure 5:
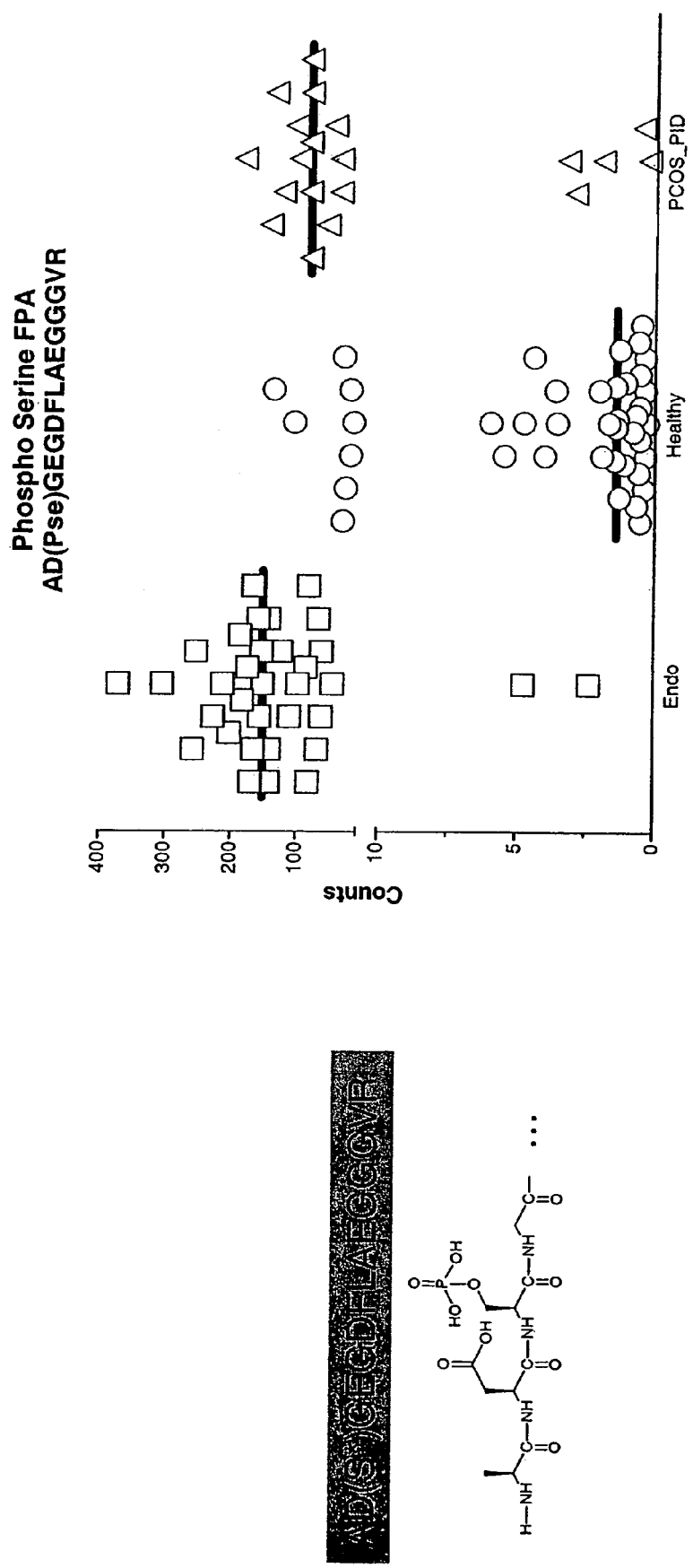
Figure 6:
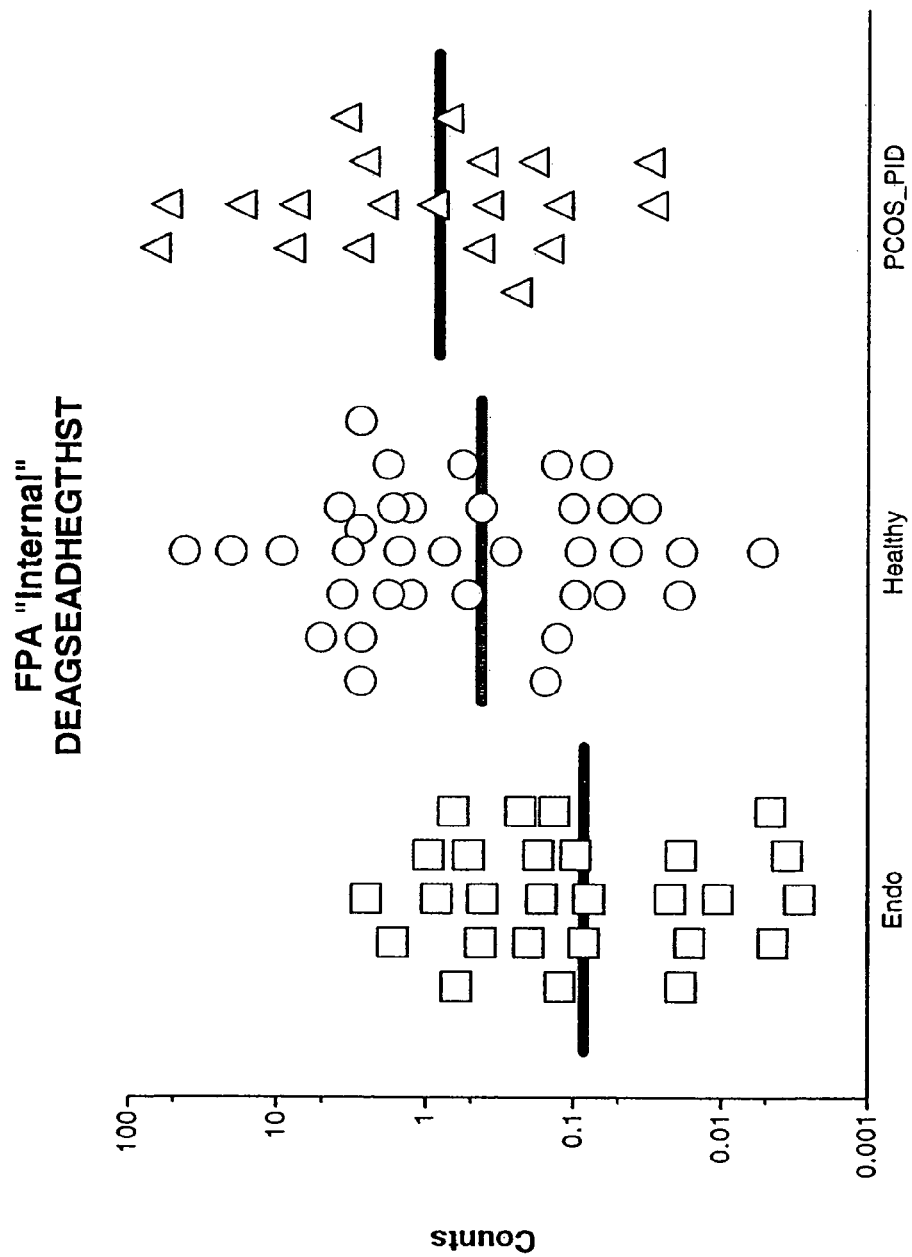

The results for several of the markers of the invention are set forth in FIGS. 1 to 6, each of which is a scatter plot showing the concentrations (given as counts) of a given marker in the serum of women diagnosed with endometriosis, the serum of healthy women, and, in certain cases, the serum of women diagnosed with PCOS or PID. The data set forth in FIGS. 1 and 2 indicate that the fibrinopeptide B derivative (SEQ ID NO:28), the full length fibrinopeptide A (SEQ ID NO:3) and the fibrinopeptide A fragment (SEQ ID NO:7) are all present in higher concentrations in the serum of women diagnosed with endometriosis than in the serum of healthy women. FIG. 3 indicates that the fibrinopeptide A derivative (SEQ ID NO:4) is present at higher concentrations in women diagnosed with endometriosis than in the serum of healthy women or women diagnosed with PCOS or PID. The data set forth in FIG. 4 demonstrate that the thymosin fragments (SEQ ID NOS:42 and 43) are present at lower concentrations in the serum of women diagnosed with endometriosis, PCOS and PID than in the serum of healthy women. FIG. 5 shows that phosphoserine fibrinopeptide A (SEQ ID NO:22) is present at lower concentrations in the serum of healthy women than in the serum of women diagnosed with endometriosis, PCOS or PID. The data in FIG. 6 demonstrate that the internal fibrinogen fragment (SEQ ID NO:29) is present at lower concentrations in the serum of women diagnosed with endometriosis than in the serum of healthy women or women diagnosed with PCOS or PID.

B. Summary of the Tables

Tables 1–3 list markers of the invention obtained using the foregoing experimental protocol. Table 1 lists all of the markers of the invention, which are over- or under-expressed in patient samples compared to normal (i.e., a sample from a patient that does not have endometriosis) samples. Table 2 lists markers whose over-expression may be correlated with endometriosis as compared to normal samples from patients that do not have endometriosis. Table 3 lists markers whose under-expression may be correlated with endometriosis as compared to normal samples from patients that do not have endometriosis.

The contents of all references, patents, published patent applications, and database records, cited throughout this application, are hereby incorporated by reference.

OTHER EMBODIMENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of assessing whether a patient is afflicted with endometriosis, the method comprising comparing:
   a) the abundance of one or more marker polypeptides selected from the group consisting of: fibrinogen α-chain (SEQ ID NO:1), or a fragment thereof; fibrinogen β-chain (SEQ ID NO:2), or a fragment thereof; ADSGEGDFLAEGGGVR (fibrinopeptide A) (SEQ ID NO:3), or a fragment thereof; GEGDFLAEGGGVR AD(dehydroA) (SEQ ID NO:4), or a fragment thereof; DSGEGDFLAEGGGVR (SEQ ID NO:5), or a fragment thereof; DSGEGDFLAEGGGV (SEQ ID NO:6), or a fragment thereof; SGEGDFLAEGGGVR (SEQ ID NO:7), or a fragment thereof; SGEGDFLAEGGGV (SEQ ID NO:8), or a fragment thereof; GEGDFLAEGGGVR (SEQ ID NO:9), or a fragment thereof; GEGDFLAEGGGV (SEQ ID NO:10), or a fragment thereof; EGDFLAEGGGVR (SEQ ID NO:11), or a fragment thereof; EGDFLAEGGGV (SEQ ID NO:12), or a fragment thereof; GDFLAEGGGVR (SEQ ID NO:13), or a fragment thereof; GDFLAEGGGV (SEQ ID NO:14), or a fragment thereof; DFLAEGGGVR (SEQ ID NO:15), or a fragment thereof; DFLAEGGGV (SEQ ID NO:16), or a fragment thereof; FLAEGGGVR (SEQ ID NO: 17), or a fragment thereof; FLAEGGGV (SEQ ID NO: 18), or a fragment thereof; LAEGGGV (SEQ ID NO: 19), or a fragment thereof; AEGGGV (SEQ ID NO:20), or a fragment thereof; EGGGV (SEQ ID NO:21), or a fragment thereof; ADS*GEGDFLAEGGGVR (phosphorylated fibrinopeptide A) (SEQ ID NO:22), or a fragment thereof; DS*GEGDFLAEGGGVR (SEQ ID NO:23), or a fragment thereof; DS*GEGDFLAEGGGV (SEQ ID NO:24), or a fragment thereof; S*GEGDFLAEGGGVR (SEQ ID NO:25), or a fragment thereof; S*GEGDFLAEGGGV (SEQ ID NO:26), or a fragment thereof; QGVNDNEEGFFSAR (fibrinopeptide B) (SEQ ID NO:27), or a fragment thereof; pyr-EGVNDNEEGFFSA (SEQ ID NO:28), or a fragment thereof; DEAGSEADHEGTHST (SEQ ID NO:29), or a fragment thereof; SVQLTEKRMDKVGKYPKELRKCCEDGMRENPMRFSCQRRTRFISLGEACKKVFLDCCN YITELRRQHARASHLGLAR (C3a) (SEQ ID NO:31), or a fragment thereof; C3b (SEQ ID NO:32), or a fragment thereof; SSKITHRIHWESASLLR (SEQ ID NO:36), or a fragment thereof; and HWESASLL (SEQ ID NO:37), or a fragment thereof, in a patient sample, wherein the fragment thereof consists of 7–15 consecutive amino acid residues of the marker polypeptide, and
   b) the normal abundance of the one or more of marker polypeptides in a sample from a control subject not afflicted with endometriosis,
   wherein a significantly greater abundance of one or more of said marker polypeptides in the patient sample as compared to the normal abundance of one or more of said marker polypeptides indicates that the patient is afflicted with endometriosis.

2. A method of assessing whether a patient is afflicted with endometriosis, the method comprising comparing:
   a) the abundance of each of a plurality of marker polypeptides independently selected from the group consisting of: fibrinogen α-chain (SEQ ID NO: 1), or a fragment thereof; fibrinogen β-chain (SEQ ID NO:2), or a fragment thereof; ADSGEGDFLAEGGGVR (fibrinopeptide A) (SEQ ID NO:3), or a fragment thereof; GEGDFLAEGGGVR AD(dehydroA) (SEQ ID NO:4), or a fragment thereof; DSGEGDFLAEGGGVR (SEQ ID NO:5), or a fragment thereof; DSGEGDFLAEGGGV (SEQ ID NO:6), or a fragment thereof; SGEGDFLAEGGGVR (SEQ ID NO:7), or a fragment thereof; SGEGDFLAEGGGV (SEQ ID NO:8), or a fragment thereof; GEGDFLAEGGGVR (SEQ ID NO:9), or a fragment thereof; GEGDFLAEGGGV (SEQ ID NO:10), or a fragment thereof; EGDFLAEGGGVR (SEQ ID NO:11), or a fragment thereof; EGDFLAEGGGV (SEQ ID NO:12), or a fragment thereof; GDFLAEGGGVR (SEQ ID NO:13), or a fragment thereof; GDFLAEGGGV (SEQ ID NO:14), or a fragment thereof; DFLAEGGGVR (SEQ ID NO:15), or a fragment thereof; DFLAEGGGV (SEQ ID NO:16), or a fragment thereof; FLAEGGGVR (SEQ ID NO: 17), or a fragment thereof; FLAEGGGV (SEQ ID NO: 18), or a fragment thereof; LAEGGGV (SEQ ID NO: 19), or a fragment thereof; AEGGGV (SEQ ID NO:20), or a fragment thereof; EGGGV (SEQ ID NO:21), or a fragment thereof; ADS*GEGDFLAEGGGVR (phosphorylated fibrinopeptide A) (SEQ ID NO:22), or a fragment thereof; DS*GEGDFLAEGGGVR (SEQ ID NO:23), or a fragment thereof; DS*GEGDFLAEGGGV (SEQ ID NO:24), or a fragment thereof; S*GEGDFLAEGGGVR (SEQ ID NO:25), or a fragment thereof; S*GEGDFLAEGGGV (SEQ ID NO:26), or a fragment thereof; QGVNDNEEGFFSAR (fibrinopeptide B) (SEQ ID NO:27), or a fragment thereof; pyr-EGVNDNEEGFFSA (SEQ ID NO:28), or a fragment thereof; DEAGSEADHEGTHST (SEQ ID NO:29), or a fragment thereof; complement component 3 (Complement C3) (SEQ ID NO:30), or a fragment thereof; SVQLTEKRMDKVGKYPKELRKCCEDGMRENPMRFSCQRRTRFISLGEACKKVFLDCCN YITELRRQHARASHLGLAR (C3a) (SEQ ID NO:31), or a fragment thereof; C3b (SEQ ID NO:32), or a fragment thereof; SSKITHRIHWESASLLR (SEQ II) NO:36), or a fragment thereof; and HWESASLL (SEQ ID NO:37), or a fragment thereof; in a patient sample, wherein the fragment thereof consists of 7–15 consecutive amino acid residues of the marker polypeptide, and
   b) the normal abundance of each of the plurality of marker polypeptides in a sample obtained from a control subject not afflicted with endometriosis,
   wherein a significantly greater abundance of one or more of said marker polypeptides in the patient sample as compared to the normal abundance of one or more of said marker polypeptides indicates that the patient is afflicted with endometnosis.

3. The method of any one of claims 1 or 2, wherein the sample comprises a fluid selected from the group consisting of blood fluids, a blood fraction, lymph, ascitic fluids, gynecological fluids, urine, peritoneal fluid, cerebrospinal fluid, and fluids collected by vaginal rinsing.

4. The method of any one of claim 1 or 2, wherein the sample is blood serum or blood plasma.

5. The method of any one of claim 1 or 2, wherein the abundance of said marker polypeptides in the samples is assessed by a method comprising the step of detecting the presence in the samples of said marker polypeptides or a fragment thereof.

6. The method of claim 5, wherein the presence of said marker polypeptide or fragment thereof is detected using a reagent which specifically binds with said marker polypeptide or fragment thereof, wherein said reagent is selected from the group consisting of an antibody, an antibody derivative, and an antibody fragment.

7. The method of claim 2, wherein the plurality comprises at least three of the marker polypeptides.

8. The method of claim 7, wherein the plurality comprises at least five of the marker polypeptides.

* * * * *

SEQUENCE LISTING

```
<160> NUMBER OF SEQ ID NOS: 44

<210> SEQ ID NO 1
<211> LENGTH: 866
<212> TYPE: PRT
<213> ORGANISM: Homo sapiens

<400> SEQUENCE: 1

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
```

```
                       20                  25                  30
Gly Val Arg Gly Pro Arg Val Val Glu Arg His Gln Ser Ala Cys Lys
             35                  40                  45

Asp Ser Asp Trp Pro Phe Cys Ser Asp Glu Asp Trp Asn Tyr Lys Cys
         50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                 85                  90                  95

Lys Asn Asn Lys Asp Ser His Ser Leu Thr Thr Asn Ile Met Glu Ile
             100                 105                 110

Leu Arg Gly Asp Phe Ser Ser Ala Asn Asn Arg Asp Asn Thr Tyr Asn
         115                 120                 125

Arg Val Ser Glu Asp Leu Arg Ser Arg Ile Glu Val Leu Lys Arg Lys
         130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                 165                 170                 175

Ile Arg Ser Cys Arg Gly Ser Cys Ser Arg Ala Leu Ala Arg Glu Val
             180                 185                 190

Asp Leu Lys Asp Tyr Glu Asp Gln Gln Lys Gln Leu Glu Gln Val Ile
         195                 200                 205

Ala Lys Asp Leu Leu Pro Ser Arg Asp Arg Gln His Leu Pro Leu Ile
         210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                 245                 250                 255

Met Arg Met Glu Leu Glu Arg Pro Gly Gly Asn Glu Ile Thr Arg Gly
             260                 265                 270

Gly Ser Thr Ser Tyr Gly Thr Gly Ser Glu Thr Glu Ser Pro Arg Asn
         275                 280                 285

Pro Ser Ser Ala Gly Ser Trp Asn Ser Gly Ser Ser Gly Pro Gly Ser
         290                 295                 300

Thr Gly Asn Arg Asn Pro Gly Ser Ser Gly Thr Gly Thr Ala Thr
305                 310                 315                 320

Trp Lys Pro Gly Ser Ser Gly Pro Gly Ser Thr Gly Ser Trp Asn Ser
                 325                 330                 335

Gly Ser Ser Gly Thr Gly Ser Thr Gly Asn Gln Asn Pro Gly Ser Pro
             340                 345                 350

Arg Pro Gly Ser Thr Gly Thr Trp Asn Pro Gly Ser Ser Glu Arg Gly
         355                 360                 365

Ser Ala Gly His Trp Thr Ser Glu Ser Ser Val Ser Gly Ser Thr Gly
         370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                 405                 410                 415

Ser Gly Asn Val Ser Pro Gly Thr Arg Arg Glu Tyr His Thr Glu Lys
             420                 425                 430

Leu Val Thr Ser Lys Gly Asp Lys Glu Leu Arg Thr Gly Lys Glu Lys
         435                 440                 445
```

```
Val Thr Ser Gly Ser Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                    485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
                580                 585                 590

Asp Ser Thr Phe Glu Ser Lys Ser Tyr Lys Met Ala Asp Glu Ala Gly
                595                 600                 605

Ser Glu Ala Asp His Glu Gly Thr His Ser Thr Lys Arg Gly His Ala
610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
                660                 665                 670

Leu Leu Ile Gln Gln Arg Met Asp Gly Ser Leu Asn Phe Asn Arg Thr
                675                 680                 685

Trp Gln Asp Tyr Lys Arg Gly Phe Gly Ser Leu Asn Asp Glu Gly Glu
                690                 695                 700

Gly Glu Phe Trp Leu Gly Asn Asp Tyr Leu His Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
                740                 745                 750

Leu Gln Val Ser Ser Tyr Glu Gly Thr Ala Gly Asp Ala Leu Ile Glu
                755                 760                 765

Gly Ser Val Glu Glu Gly Ala Glu Tyr Thr Ser His Asn Asn Met Gln
770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
                820                 825                 830

Ser Pro Tyr Glu Ile Glu Asn Gly Val Val Trp Val Ser Phe Arg Gly
                835                 840                 845

Ala Asp Tyr Ser Leu Arg Ala Val Arg Met Lys Ile Arg Pro Leu Val
850                 855                 860
```

```
Thr Gln
865

<210> SEQ ID NO 2
<211> LENGTH: 491
<212> TYPE: PRT
<213> ORGANISM: Homo sapiens

<400> SEQUENCE: 2

Met Lys Arg Met Val Ser Trp Ser Phe His Lys Leu Lys Thr Met Lys
 1               5                  10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
        50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
        290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365
```

```
Gln Ile Ser Val Asn Lys Tyr Arg Gly Thr Ala Gly Asn Ala Leu Met
        370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Trp
            420                 425                 430

Trp Tyr Asn Arg Cys His Ala Ala Asn Pro Asn Gly Arg Tyr Tyr Trp
                435                 440                 445

Gly Gly Gln Tyr Thr Trp Asp Met Ala Lys His Gly Thr Asp Asp Gly
        450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 3
<211> LENGTH: 16
<212> TYPE: PRT
<213> ORGANISM: Homo sapiens

<400> SEQUENCE: 3

Ala Asp Ser Gly Glu Gly Asp Phe Leu Ala Glu Gly Gly Gly Val Arg
1               5                   10                  15

<210> SEQ ID NO 4
<211> LENGTH: 16
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Dehydroalanine

<400> SEQUENCE: 4

Ala Asp Xaa Gly Glu Gly Asp Phe Leu Ala Glu Gly Gly Gly Val Arg
1               5                   10                  15

<210> SEQ ID NO 5
<211> LENGTH: 15
<212> TYPE: PRT
<213> ORGANISM: Homo sapiens

<400> SEQUENCE: 5

Asp Ser Gly Glu Gly Asp Phe Leu Ala Glu Gly Gly Gly Val Arg
1               5                   10                  15

<210> SEQ ID NO 6
<211> LENGTH: 14
<212> TYPE: PRT
<213> ORGANISM: Homo sapiens

<400> SEQUENCE: 6

Asp Ser Gly Glu Gly Asp Phe Leu Ala Glu Gly Gly Gly Val
1               5                   10

<210> SEQ ID NO 7
<211> LENGTH: 14
<212> TYPE: PRT
<213> ORGANISM: Homo sapiens
```

<400> SEQUENCE: 7

Ser Gly Glu Gly Asp Phe Leu Ala Glu Gly Gly Gly Val Arg
 1               5                  10

<210> SEQ ID NO 8
<211> LENGTH: 13
<212> TYPE: PRT
<213> ORGANISM: Homo sapiens

<400> SEQUENCE: 8

Ser Gly Glu Gly Asp Phe Leu Ala Glu Gly Gly Gly Val
 1               5                  10

<210> SEQ ID NO 9
<211> LENGTH: 13
<212> TYPE: PRT
<213> ORGANISM: Homo sapiens

<400> SEQUENCE: 9

Gly Glu Gly Asp Phe Leu Ala Glu Gly Gly Gly Val Arg
 1               5                  10

<210> SEQ ID NO 10
<211> LENGTH: 12
<212> TYPE: PRT
<213> ORGANISM: Homo sapiens

<400> SEQUENCE: 10

Gly Glu Gly Asp Phe Leu Ala Glu Gly Gly Gly Val
 1               5                  10

<210> SEQ ID NO 11
<211> LENGTH: 12
<212> TYPE: PRT
<213> ORGANISM: Homo sapiens

<400> SEQUENCE: 11

Glu Gly Asp Phe Leu Ala Glu Gly Gly Gly Val Arg
 1               5                  10

<210> SEQ ID NO 12
<211> LENGTH: 11
<212> TYPE: PRT
<213> ORGANISM: Homo sapiens

<400> SEQUENCE: 12

Glu Gly Asp Phe Leu Ala Glu Gly Gly Gly Val
 1               5                  10

<210> SEQ ID NO 13
<211> LENGTH: 11
<212> TYPE: PRT
<213> ORGANISM: Homo sapiens

<400> SEQUENCE: 13

Gly Asp Phe Leu Ala Glu Gly Gly Gly Val Arg
 1               5                  10

<210> SEQ ID NO 14
<211> LENGTH: 10
<212> TYPE: PRT
<213> ORGANISM: Homo sapiens

<400> SEQUENCE: 14

```
Gly Asp Phe Leu Ala Glu Gly Gly Gly Val
 1               5                   10

<210> SEQ ID NO 15
<211> LENGTH: 10
<212> TYPE: PRT
<213> ORGANISM: Homo sapiens

<400> SEQUENCE: 15

Asp Phe Leu Ala Glu Gly Gly Gly Val Arg
 1               5                   10

<210> SEQ ID NO 16
<211> LENGTH: 9
<212> TYPE: PRT
<213> ORGANISM: Homo sapiens

<400> SEQUENCE: 16

Asp Phe Leu Ala Glu Gly Gly Gly Val
 1               5

<210> SEQ ID NO 17
<211> LENGTH: 9
<212> TYPE: PRT
<213> ORGANISM: Homo sapiens

<400> SEQUENCE: 17

Phe Leu Ala Glu Gly Gly Gly Val Arg
 1               5

<210> SEQ ID NO 18
<211> LENGTH: 8
<212> TYPE: PRT
<213> ORGANISM: Homo sapiens

<400> SEQUENCE: 18

Phe Leu Ala Glu Gly Gly Gly Val
 1               5

<210> SEQ ID NO 19
<211> LENGTH: 7
<212> TYPE: PRT
<213> ORGANISM: Homo sapiens

<400> SEQUENCE: 19

Leu Ala Glu Gly Gly Gly Val
 1               5

<210> SEQ ID NO 20
<211> LENGTH: 6
<212> TYPE: PRT
<213> ORGANISM: Homo sapiens

<400> SEQUENCE: 20

Ala Glu Gly Gly Gly Val
 1               5

<210> SEQ ID NO 21
<211> LENGTH: 5
<212> TYPE: PRT
<213> ORGANISM: Homo sapiens

<400> SEQUENCE: 21

Glu Gly Gly Gly Val
 1               5
```

```
<210> SEQ ID NO 22
<211> LENGTH: 16
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Phosphoserine

<400> SEQUENCE: 22

Ala Asp Xaa Glu Glu Gly Asp Phe Leu Ala Glu Gly Gly Gly Val Arg
 1               5                  10                  15

<210> SEQ ID NO 23
<211> LENGTH: 15
<212> TYPE: PRT
<213> ORGANISM: Homo sapiens
<220> FEATURE:
<221> NAME/KEY: VARIANT
<222> LOCATION: 2
<223> OTHER INFORMATION: Xaa = Phosphoserine

<400> SEQUENCE: 23

Asp Xaa Gly Glu Gly Asp Phe Leu Ala Glu Gly Gly Gly Val Arg
 1               5                  10                  15

<210> SEQ ID NO 24
<211> LENGTH: 14
<212> TYPE: PRT
<213> ORGANISM: Homo sapiens
<220> FEATURE:
<221> NAME/KEY: VARIANT
<222> LOCATION: 2
<223> OTHER INFORMATION: Xaa = Phosphoserine

<400> SEQUENCE: 24

Asp Xaa Gly Glu Gly Asp Phe Leu Ala Glu Gly Gly Gly Val
 1               5                  10

<210> SEQ ID NO 25
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Phosphoserine

<400> SEQUENCE: 25

Xaa Gly Glu Gly Asp Phe Leu Ala Glu Gly Gly Gly Val Arg
 1               5                  10

<210> SEQ ID NO 26
<211> LENGTH: 13
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Phosphoserine

<400> SEQUENCE: 26

Xaa Gly Glu Gly Asp Phe Leu Ala Glu Gly Gly Gly Val
 1               5                  10

<210> SEQ ID NO 27
<211> LENGTH: 14
```

```
<212> TYPE: PRT
<213> ORGANISM: Homo sapiens

<400> SEQUENCE: 27

Gln Gly Val Asn Asp Asn Glu Glu Gly Phe Phe Ser Ala Arg
 1               5                  10

<210> SEQ ID NO 28
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Pyroglutamate

<400> SEQUENCE: 28

Xaa Glu Gly Val Asn Asp Asn Glu Glu Gly Phe Phe Ser Ala
 1               5                  10

<210> SEQ ID NO 29
<211> LENGTH: 15
<212> TYPE: PRT
<213> ORGANISM: Homo sapiens

<400> SEQUENCE: 29

Asp Glu Ala Gly Ser Glu Ala Asp His Glu Gly Thr His Ser Thr
 1               5                  10                  15

<210> SEQ ID NO 30
<211> LENGTH: 1663
<212> TYPE: PRT
<213> ORGANISM: Homo sapiens

<400> SEQUENCE: 30

Met Gly Pro Thr Ser Gly Pro Ser Leu Leu Leu Leu Leu Thr His
 1               5                  10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Leu Val Ser Leu Gln Ser Gly
        115                 120                 125

Tyr Leu Phe Ile Gln Thr Asp Lys Thr Ile Tyr Thr Pro Gly Ser Thr
        130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
```

-continued

```
            195                 200                 205
Tyr Tyr Glu Asn Ser Pro Gln Gln Val Phe Ser Thr Glu Phe Glu Val
        210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
                260                 265                 270
Phe Gly Ile Gln Asp Gly Glu Gln Arg Ile Ser Leu Pro Glu Ser Leu
                275                 280                 285
Lys Arg Ile Pro Ile Glu Asp Gly Ser Gly Glu Val Val Leu Ser Arg
290                 295                 300
Lys Val Leu Leu Asp Gly Val Gln Asn Leu Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
                355                 360                 365
Pro Phe Asp Leu Met Val Phe Val Thr Asn Pro Asp Gly Ser Pro Ala
370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
                435                 440                 445
Val Gly Asn Ser Asn Asn Tyr Leu His Leu Ser Val Leu Arg Thr Glu
        450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
                500                 505                 510
Asp Leu Val Val Leu Pro Leu Ser Ile Thr Thr Asp Phe Ile Pro Ser
                515                 520                 525
Phe Arg Leu Val Ala Tyr Tyr Thr Leu Ile Gly Ala Ser Gly Gln Arg
        530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
                580                 585                 590
Val Val Leu Val Ala Val Asp Lys Gly Val Phe Val Leu Asn Lys Lys
        595                 600                 605
Asn Lys Leu Thr Gln Ser Lys Ile Trp Asp Val Val Glu Lys Ala Asp
        610                 615                 620
```

-continued

```
Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
            645                 650                 655

Arg Ala Glu Leu Gln Cys Pro Gln Pro Ala Ala Arg Arg Arg Ser
                660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Asn Ile Val Ser Arg Ser Glu Phe Pro
            755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Arg Asn Glu Gln Val Glu Ile Arg
            835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
            930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
            995                 1000                1005

Gly Cys Gly Glu Gln Asn Met Ile Gly Met Thr Pro Thr Val Ile Ala
        1010                1015                1020

Val His Tyr Leu Asp Glu Thr Glu Gln Trp Glu Lys Phe Gly Leu Glu
1025                1030                1035                1040
```

-continued

Lys Arg Gln Gly Ala Leu Glu Leu Ile Lys Lys Gly Tyr Thr Gln Gln
             1045                1050                1055

Leu Ala Phe Arg Gln Pro Ser Ser Ala Phe Ala Ala Phe Val Lys Arg
             1060                1065                1070

Ala Pro Ser Thr Trp Leu Thr Ala Tyr Val Val Lys Val Phe Ser Leu
             1075                1080                1085

Ala Val Asn Leu Ile Ala Ile Asp Ser Gln Val Leu Cys Gly Ala Val
             1090                1095                1100

Lys Trp Leu Ile Leu Glu Lys Gln Lys Pro Asp Gly Val Phe Gln Glu
1105                1110                1115                1120

Asp Ala Pro Val Ile His Gln Glu Met Ile Gly Gly Leu Arg Asn Asn
             1125                1130                1135

Asn Glu Lys Asp Met Ala Leu Thr Ala Phe Val Leu Ile Ser Leu Gln
             1140                1145                1150

Glu Ala Lys Asp Ile Cys Glu Glu Gln Val Asn Ser Leu Pro Gly Ser
             1155                1160                1165

Ile Thr Lys Ala Gly Asp Phe Leu Glu Ala Asn Tyr Met Asn Leu Gln
             1170                1175                1180

Arg Ser Tyr Thr Val Ala Ile Ala Gly Tyr Ala Leu Ala Gln Met Gly
1185                1190                1195                1200

Arg Leu Lys Gly Pro Leu Leu Asn Lys Phe Leu Thr Thr Ala Lys Asp
             1205                1210                1215

Lys Asn Arg Trp Glu Asp Pro Gly Lys Gln Leu Tyr Asn Val Glu Ala
             1220                1225                1230

Thr Ser Tyr Ala Leu Leu Ala Leu Leu Gln Leu Lys Asp Phe Asp Phe
             1235                1240                1245

Val Pro Pro Val Val Arg Trp Leu Asn Glu Gln Arg Tyr Tyr Gly Gly
             1250                1255                1260

Gly Tyr Gly Ser Thr Gln Ala Thr Phe Met Val Phe Gln Ala Leu Ala
1265                1270                1275                1280

Gln Tyr Gln Lys Asp Ala Pro Asp His Gln Glu Leu Asn Leu Asp Val
             1285                1290                1295

Ser Leu Gln Leu Pro Ser Arg Ser Ser Lys Ile Thr His Arg Ile His
             1300                1305                1310

Trp Glu Ser Ala Ser Leu Leu Arg Ser Glu Glu Thr Lys Glu Asn Glu
             1315                1320                1325

Gly Phe Thr Val Thr Ala Glu Gly Lys Gly Gln Gly Thr Leu Ser Val
             1330                1335                1340

Val Thr Met Tyr His Ala Lys Ala Lys Asp Gln Leu Thr Cys Asn Lys
1345                1350                1355                1360

Phe Asp Leu Lys Val Thr Ile Lys Pro Ala Pro Glu Thr Glu Lys Arg
             1365                1370                1375

Pro Gln Asp Ala Lys Asn Thr Met Ile Leu Glu Ile Cys Thr Arg Tyr
             1380                1385                1390

Arg Gly Asp Gln Asp Ala Thr Met Ser Ile Leu Asp Ile Ser Met Met
             1395                1400                1405

Thr Gly Phe Ala Pro Asp Thr Asp Asp Leu Lys Gln Leu Ala Asn Gly
             1410                1415                1420

Val Asp Arg Tyr Ile Ser Lys Tyr Glu Leu Asp Lys Ala Phe Ser Asp
1425                1430                1435                1440

Arg Asn Thr Leu Ile Ile Tyr Leu Asp Lys Val Ser His Ser Glu Asp
             1445                1450                1455

Asp Cys Leu Ala Phe Lys Val His Gln Tyr Phe Asn Val Glu Leu Ile

```
                    1460               1465               1470
Gln Pro Gly Ala Val Lys Val Tyr Ala Tyr Tyr Asn Leu Glu Glu Ser
        1475                1480                1485

Cys Thr Arg Phe Tyr His Pro Glu Lys Glu Asp Gly Lys Leu Asn Lys
    1490                1495                1500

Leu Cys Arg Asp Glu Leu Cys Arg Cys Ala Glu Glu Asn Cys Phe Ile
1505                1510                1515                1520

Gln Lys Ser Asp Asp Lys Val Thr Leu Glu Glu Arg Leu Asp Lys Ala
                1525                1530                1535

Cys Glu Pro Gly Val Asp Tyr Val Tyr Lys Thr Arg Leu Val Lys Val
            1540                1545                1550

Gln Leu Ser Asn Asp Phe Asp Glu Tyr Ile Met Ala Ile Glu Gln Thr
                1555                1560                1565

Ile Lys Ser Gly Ser Asp Glu Val Gln Val Gly Gln Gln Arg Thr Phe
1570                1575                1580

Ile Ser Pro Ile Lys Cys Arg Glu Ala Leu Lys Leu Glu Glu Lys Lys
1585                1590                1595                1600

His Tyr Leu Met Trp Gly Leu Ser Ser Asp Phe Trp Gly Glu Lys Pro
                1605                1610                1615

Asn Leu Ser Tyr Ile Ile Gly Lys Asp Thr Trp Val Glu His Trp Pro
                1620                1625                1630

Glu Glu Asp Glu Cys Gln Asp Glu Glu Asn Gln Lys Gln Cys Gln Asp
            1635                1640                1645

Leu Gly Ala Phe Thr Glu Ser Met Val Val Phe Gly Cys Pro Asn
        1650                1655                1660

<210> SEQ ID NO 31
<211> LENGTH: 77
<212> TYPE: PRT
<213> ORGANISM: Homo sapiens

<400> SEQUENCE: 31

Ser Val Gln Leu Thr Glu Lys Arg Met Asp Lys Val Gly Lys Tyr Pro
1               5                  10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75

<210> SEQ ID NO 32
<211> LENGTH: 935
<212> TYPE: PRT
<213> ORGANISM: Homo sapiens

<400> SEQUENCE: 32

Asn Tyr Ile Thr Glu Leu Arg Arg Gln His Ala Arg Ala Ser His Leu
1               5                  10                  15

Gly Leu Ala Arg Ser Asn Leu Asp Glu Asp Ile Ile Ala Glu Glu Asn
            20                  25                  30

Ile Val Ser Arg Ser Glu Phe Pro Glu Ser Trp Leu Trp Asn Val Glu
        35                  40                  45

Asp Leu Lys Glu Pro Pro Lys Asn Gly Ile Ser Thr Lys Leu Met Asn
```

-continued

```
                 50                  55                  60
Ile Phe Leu Lys Asp Ser Ile Thr Thr Trp Glu Ile Leu Ala Val Ser
 65                  70                  75                  80

Met Ser Asp Lys Lys Gly Ile Cys Val Ala Asp Pro Phe Glu Val Thr
                 85                  90                  95

Val Met Gln Asp Phe Phe Ile Asp Leu Arg Leu Pro Tyr Ser Val Val
                100                 105                 110

Arg Asn Glu Gln Val Glu Ile Arg Ala Val Leu Tyr Asn Tyr Arg Gln
                115                 120                 125

Asn Gln Glu Leu Lys Val Arg Val Glu Leu Leu His Asn Pro Ala Phe
130                 135                 140

Cys Ser Leu Ala Thr Thr Lys Arg Arg His Gln Gln Thr Val Thr Ile
145                 150                 155                 160

Pro Pro Lys Ser Ser Leu Ser Val Pro Tyr Val Ile Val Pro Leu Lys
                165                 170                 175

Thr Gly Leu Gln Glu Val Glu Val Lys Ala Ala Val Tyr His His Phe
                180                 185                 190

Ile Ser Asp Gly Val Arg Lys Ser Leu Lys Val Pro Glu Gly Ile
                195                 200                 205

Arg Met Asn Lys Thr Val Ala Val Arg Thr Leu Asp Pro Glu Arg Leu
210                 215                 220

Gly Arg Glu Gly Val Gln Lys Glu Asp Ile Pro Pro Ala Asp Leu Ser
225                 230                 235                 240

Asp Gln Val Pro Asp Thr Glu Ser Glu Thr Arg Ile Leu Leu Gln Gly
                245                 250                 255

Thr Pro Val Ala Gln Met Thr Glu Asp Ala Val Asp Ala Glu Arg Leu
                260                 265                 270

Lys His Leu Ile Val Thr Pro Ser Gly Cys Gly Glu Gln Asn Met Ile
                275                 280                 285

Gly Met Thr Pro Thr Val Ile Ala Val His Tyr Leu Asp Glu Thr Glu
                290                 295                 300

Gln Trp Glu Lys Phe Gly Leu Glu Lys Arg Gln Gly Ala Leu Glu Leu
305                 310                 315                 320

Ile Lys Lys Gly Tyr Thr Gln Gln Leu Ala Phe Arg Gln Pro Ser Ser
                325                 330                 335

Ala Phe Ala Ala Phe Val Lys Arg Ala Pro Ser Thr Trp Leu Thr Ala
                340                 345                 350

Tyr Val Val Lys Val Phe Ser Leu Ala Val Asn Leu Ile Ala Ile Asp
                355                 360                 365

Ser Gln Val Leu Cys Gly Ala Val Lys Trp Leu Ile Leu Glu Lys Gln
370                 375                 380

Lys Pro Asp Gly Val Phe Gln Glu Asp Ala Pro Val Ile His Gln Glu
385                 390                 395                 400

Met Ile Gly Gly Leu Arg Asn Asn Asn Glu Lys Asp Met Ala Leu Thr
                405                 410                 415

Ala Phe Val Leu Ile Ser Leu Gln Glu Ala Lys Asp Ile Cys Glu Glu
                420                 425                 430

Gln Val Asn Ser Leu Pro Gly Ser Ile Thr Lys Ala Gly Asp Phe Leu
                435                 440                 445

Glu Ala Asn Tyr Met Asn Leu Gln Arg Ser Tyr Thr Val Ala Ile Ala
                450                 455                 460

Gly Tyr Ala Leu Ala Gln Met Gly Arg Leu Lys Gly Pro Leu Leu Asn
465                 470                 475                 480
```

```
Lys Phe Leu Thr Thr Ala Lys Asp Lys Asn Arg Trp Glu Asp Pro Gly
                485                 490                 495

Lys Gln Leu Tyr Asn Val Glu Ala Thr Ser Tyr Ala Leu Leu Ala Leu
            500                 505                 510

Leu Gln Leu Lys Asp Phe Asp Phe Val Pro Pro Val Arg Trp Leu
        515                 520                 525

Asn Glu Gln Arg Tyr Tyr Gly Gly Tyr Gly Ser Thr Gln Ala Thr
530                 535                 540

Phe Met Val Phe Gln Ala Leu Ala Gln Tyr Gln Lys Asp Ala Pro Asp
545                 550                 555                 560

His Gln Glu Leu Asn Leu Asp Val Ser Leu Gln Leu Pro Ser Arg Ser
                565                 570                 575

Ser Lys Ile Thr His Arg Ile His Trp Glu Ser Ala Ser Leu Leu Arg
            580                 585                 590

Ser Glu Glu Thr Lys Glu Asn Glu Gly Phe Thr Val Thr Ala Glu Gly
        595                 600                 605

Lys Gly Gln Gly Thr Leu Ser Val Val Thr Met Tyr His Ala Lys Ala
    610                 615                 620

Lys Asp Gln Leu Thr Cys Asn Lys Phe Asp Leu Lys Val Thr Ile Lys
625                 630                 635                 640

Pro Ala Pro Glu Thr Glu Lys Arg Pro Gln Asp Ala Lys Asn Thr Met
                645                 650                 655

Ile Leu Glu Ile Cys Thr Arg Tyr Arg Gly Asp Gln Asp Ala Thr Met
            660                 665                 670

Ser Ile Leu Asp Ile Ser Met Met Thr Gly Phe Ala Pro Asp Thr Asp
        675                 680                 685

Asp Leu Lys Gln Leu Ala Asn Gly Val Asp Arg Tyr Ile Ser Lys Tyr
    690                 695                 700

Glu Leu Asp Lys Ala Phe Ser Asp Arg Asn Thr Leu Ile Ile Tyr Leu
705                 710                 715                 720

Asp Lys Val Ser His Ser Glu Asp Asp Cys Leu Ala Phe Lys Val His
                725                 730                 735

Gln Tyr Phe Asn Val Glu Leu Ile Gln Pro Gly Ala Val Lys Val Tyr
            740                 745                 750

Ala Tyr Tyr Asn Leu Glu Glu Ser Cys Thr Arg Phe Tyr His Pro Glu
        755                 760                 765

Lys Glu Asp Gly Lys Leu Asn Lys Leu Cys Arg Asp Glu Leu Cys Arg
    770                 775                 780

Cys Ala Glu Glu Asn Cys Phe Ile Gln Lys Ser Asp Asp Lys Val Thr
785                 790                 795                 800

Leu Glu Glu Arg Leu Asp Lys Ala Cys Glu Pro Gly Val Asp Tyr Val
                805                 810                 815

Tyr Lys Thr Arg Leu Val Lys Val Gln Leu Ser Asn Asp Phe Asp Glu
            820                 825                 830

Tyr Ile Met Ala Ile Glu Gln Thr Ile Lys Ser Gly Ser Asp Glu Val
        835                 840                 845

Gln Val Gly Gln Gln Arg Thr Phe Ile Ser Pro Ile Lys Cys Arg Glu
    850                 855                 860

Ala Leu Lys Leu Glu Glu Lys Lys His Tyr Leu Met Trp Gly Leu Ser
865                 870                 875                 880

Ser Asp Phe Trp Gly Glu Lys Pro Asn Leu Ser Tyr Ile Ile Gly Lys
                885                 890                 895
```

```
Asp Thr Trp Val Glu His Trp Pro Glu Glu Asp Glu Cys Gln Asp Glu
            900                 905                 910

Glu Asn Gln Lys Gln Cys Gln Asp Leu Gly Ala Phe Thr Glu Ser Met
        915                 920                 925

Val Val Phe Gly Cys Pro Asn
    930                 935

<210> SEQ ID NO 33
<211> LENGTH: 343
<212> TYPE: PRT
<213> ORGANISM: Homo sapiens

<400> SEQUENCE: 33

Ser Glu Glu Thr Lys Glu Asn Glu Gly Phe Thr Val Thr Ala Glu Gly
  1               5                  10                  15

Lys Gly Gln Gly Thr Leu Ser Val Val Thr Met Tyr His Ala Lys Ala
             20                  25                  30

Lys Asp Gln Leu Thr Cys Asn Lys Phe Asp Leu Lys Val Thr Ile Lys
         35                  40                  45

Pro Ala Pro Glu Thr Glu Lys Arg Pro Gln Asp Ala Lys Asn Thr Met
     50                  55                  60

Ile Leu Glu Ile Cys Thr Arg Tyr Arg Gly Asp Gln Asp Ala Thr Met
 65                  70                  75                  80

Ser Ile Leu Asp Ile Ser Met Met Thr Gly Phe Ala Pro Asp Thr Asp
                 85                  90                  95

Asp Leu Lys Gln Leu Ala Asn Gly Val Asp Arg Tyr Ile Ser Lys Tyr
            100                 105                 110

Glu Leu Asp Lys Ala Phe Ser Asp Arg Asn Thr Leu Ile Ile Tyr Leu
        115                 120                 125

Asp Lys Val Ser His Ser Glu Asp Asp Cys Leu Ala Phe Lys Val His
130                 135                 140

Gln Tyr Phe Asn Val Glu Leu Ile Gln Pro Gly Ala Val Lys Val Tyr
145                 150                 155                 160

Ala Tyr Tyr Asn Leu Glu Glu Ser Cys Thr Arg Phe Tyr His Pro Glu
                165                 170                 175

Lys Glu Asp Gly Lys Leu Asn Lys Leu Cys Arg Asp Glu Leu Cys Arg
            180                 185                 190

Cys Ala Glu Glu Asn Cys Phe Ile Gln Lys Ser Asp Asp Lys Val Thr
        195                 200                 205

Leu Glu Glu Arg Leu Asp Lys Ala Cys Glu Pro Gly Val Asp Tyr Val
    210                 215                 220

Tyr Lys Thr Arg Leu Val Lys Val Gln Leu Ser Asn Asp Phe Asp Glu
225                 230                 235                 240

Tyr Ile Met Ala Ile Glu Gln Thr Ile Lys Ser Gly Ser Asp Glu Val
                245                 250                 255

Gln Val Gly Gln Gln Arg Thr Phe Ile Ser Pro Ile Lys Cys Arg Glu
            260                 265                 270

Ala Leu Lys Leu Glu Glu Lys Lys His Tyr Leu Met Trp Gly Leu Ser
        275                 280                 285

Ser Asp Phe Trp Gly Glu Lys Pro Asn Leu Ser Tyr Ile Ile Gly Lys
    290                 295                 300

Asp Thr Trp Val Glu His Trp Pro Glu Glu Asp Glu Cys Gln Asp Glu
305                 310                 315                 320

Glu Asn Gln Lys Gln Cys Gln Asp Leu Gly Ala Phe Thr Glu Ser Met
                325                 330                 335
```

```
Val Val Phe Gly Cys Pro Asn
            340

<210> SEQ ID NO 34
<211> LENGTH: 16
<212> TYPE: PRT
<213> ORGANISM: Homo sapiens

<400> SEQUENCE: 34

Ser Glu Glu Thr Lys Glu Asn Glu Gly Phe Thr Val Thr Ala Glu Gly
1               5                   10                  15

<210> SEQ ID NO 35
<211> LENGTH: 15
<212> TYPE: PRT
<213> ORGANISM: Homo sapiens

<400> SEQUENCE: 35

Glu Glu Thr Lys Glu Asn Glu Gly Phe Thr Val Thr Ala Glu Gly
1               5                   10                  15

<210> SEQ ID NO 36
<211> LENGTH: 17
<212> TYPE: PRT
<213> ORGANISM: Homo sapiens

<400> SEQUENCE: 36

Ser Ser Lys Ile Thr His Arg Ile His Trp Glu Ser Ala Ser Leu Leu
1               5                   10                  15

Arg

<210> SEQ ID NO 37
<211> LENGTH: 8
<212> TYPE: PRT
<213> ORGANISM: Homo sapiens

<400> SEQUENCE: 37

His Trp Glu Ser Ala Ser Leu Leu
1               5

<210> SEQ ID NO 38
<211> LENGTH: 43
<212> TYPE: PRT
<213> ORGANISM: Homo sapiens

<400> SEQUENCE: 38

Ser Asp Lys Pro Asp Met Ala Glu Met Glu Lys Phe Asp Lys Ser Lys
1               5                   10                  15

Leu Lys Lys Thr Glu Thr Gln Glu Lys Asn Pro Leu Pro Ser Lys Glu
                20                  25                  30

Thr Ile Glu Gln Glu Lys Gln Ala Gly Glu Ser
            35                  40

<210> SEQ ID NO 39
<211> LENGTH: 43
<212> TYPE: PRT
<213> ORGANISM: Homo sapiens

<400> SEQUENCE: 39

Ser Asp Lys Pro Asp Met Ala Glu Ile Glu Lys Phe Asp Lys Pro Lys
1               5                   10                  15

Leu Lys Lys Thr Glu Thr Gln Glu Lys Asn Pro Leu Pro Ser Lys Glu
```

```
                20                  25                  30
Thr Ile Glu Gln Glu Lys Gln Ala Gly Glu Ser
            35                  40

<210> SEQ ID NO 40
<211> LENGTH: 44
<212> TYPE: PRT
<213> ORGANISM: Homo sapiens

<400> SEQUENCE: 40

Met Ser Asp Lys Pro Asp Met Ala Glu Ile Glu Lys Phe Asp Lys Ser
 1               5                  10                  15

Lys Leu Lys Lys Thr Glu Thr Gln Glu Lys Asn Pro Leu Pro Ser Lys
                20                  25                  30

Glu Thr Ile Glu Gln Glu Lys Gln Ala Gly Glu Ser
            35                  40

<210> SEQ ID NO 41
<211> LENGTH: 43
<212> TYPE: PRT
<213> ORGANISM: Homo sapiens

<400> SEQUENCE: 41

Ser Asp Lys Ser Asp Met Ala Glu Ile Glu Lys Phe Asp Lys Ser Lys
 1               5                  10                  15

Leu Lys Lys Thr Glu Thr Gln Glu Lys Asn Pro Leu Pro Ser Lys Glu
                20                  25                  30

Thr Ile Glu Gln Glu Lys Gln Ala Gly Glu Ser
            35                  40

<210> SEQ ID NO 42
<211> LENGTH: 22
<212> TYPE: PRT
<213> ORGANISM: Homo sapiens

<400> SEQUENCE: 42

Thr Gln Glu Lys Asn Pro Leu Pro Ser Lys Glu Thr Ile Glu Gln Glu
 1               5                  10                  15

Lys Gln Ala Gly Glu Ser
            20

<210> SEQ ID NO 43
<211> LENGTH: 21
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Pyroglutamate

<400> SEQUENCE: 43

Xaa Glu Lys Asn Pro Leu Pro Ser Lys Glu Thr Ile Glu Gln Glu Lys
 1               5                  10                  15

Gln Ala Gly Glu Ser
            20

<210> SEQ ID NO 44
<211> LENGTH: 13
<212> TYPE: PRT
<213> ORGANISM: Homo sapiens

<400> SEQUENCE: 44
```

-continued

```
Glu Gly Leu Asn Asp Asn Glu Glu Gly Phe Phe Ser Ala
1               5                   10
```